(12) United States Patent
Hawiger et al.

(10) Patent No.: US 9,388,224 B2
(45) Date of Patent: Jul. 12, 2016

(54) COMPOSITIONS FOR PRESERVING INSULIN-PRODUCING CELLS AND INSULIN PRODUCTION AND TREATING DIABETES

(71) Applicant: VANDERBILT UNIVERSITY, Nashville, TN (US)

(72) Inventors: Jack J. Hawiger, Nashville, TN (US); Daniel J. Moore, Nashville, TN (US); Jozef Zienkiewicz, Nashville, TN (US); Ruth Ann Veach, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/593,644

(22) Filed: Jan. 9, 2015

(65) Prior Publication Data

US 2015/0191522 A1    Jul. 9, 2015

Related U.S. Application Data

(63) Continuation-in-part of application No. 13/645,754, filed on Oct. 5, 2012, now Pat. No. 8,932,559.

(60) Provisional application No. 61/544,018, filed on Oct. 6, 2011.

(51) Int. Cl.
*A61K 38/00* (2006.01)
*C07K 14/47* (2006.01)

(52) U.S. Cl.
CPC .............. *C07K 14/4702* (2013.01); *A61K 38/00* (2013.01); *C07K 2319/10* (2013.01)

(58) Field of Classification Search
None
See application file for complete search history.

(56) References Cited

U.S. PATENT DOCUMENTS 6,495,518 B1 * 12/2002 Hawiger ............ A61K 38/1709 514/1.2
2004/0147435 A1 * 7/2004 Hawiger ............ A61K 38/1709 424/185.1

OTHER PUBLICATIONS

Liu et al, Peptide-directed Suppression of a Pro-inflammatory Cytokine Response (J Biol Chem. Jun. 2, 2000;275(22)16774-8).*

Z. Yang et al.: "Combined treatment with lisofylline and exendin-4 reverses autoimmune diabetes", Biochem Biophys Res Commun. Jun. 9, 2006;344(3):1017-22. Epub Apr. 5, 2006.
N. Soltani et al: "GABA exerts protective and regenerative effects on islet beta cells and reverses diabetes", Proc Natl Acad Sci U S A. Jul. 12, 2011;108(28):11692-7. doi: 10.1073/pnas.1102715108. Epub Jun. 27, 2011.
H. Kaneto et al.: "Possible novel therapy for diabetes with cell-permeable JNK-inhibitory peptide", Nat Med. Oct. 2004;10(10):1128-32. Epub Sep. 26, 2004.
V. Ablamunits et al.: "Islet T cells secreting IFN-gamma in NOD mouse diabetes: arrest by p277 peptide treatment", J Autoimmun. Feb. 1998;11(1):73-81.
T. Fujita et al.: "Reduction of insulin resistance in obese and/or diabetic animals by 5-[4-(1-methylcyclohexylmethoxy)benzyl]-thiazolidine-2,4-dione (ADD-3878, U-63,287, ciglitazone), a new antidiabetic agent", Diabetes. Sep. 1983;32(9):804-10.
R. W. Stevenson et al.: "Actions of novel antidiabetic agent englitazone in hyperglycemic hyperinsulinemic ob/ob mice", Diabetes. Oct. 1990;39(10):1218-27.
W. Sun et al.: "Intramuscular transfer of naked calcitonin gene-related peptide gene prevents autoimmune diabetes induced by multiple low-dose streptozotocin in C57BL mice", Eur J Immunol. Jan. 2003;33(1):233-42.
J.F. Todd et al.: "Incretins and other peptides in the treatment of diabetes", Diabet Med. Mar. 2007;24(3):223-32.

* cited by examiner

*Primary Examiner* — James H Alstrum Acevedo
*Assistant Examiner* — Sergio Coffa
(74) *Attorney, Agent, or Firm* — Meunier Carlin & Curfman LLC

(57) ABSTRACT

Nuclear Transport Modifiers such as cSN50 and cSN50.1, afford in vivo islet protection following a 2-day course of intense treatment in autoimmune diabetes-prone, non-obese diabetic (NOD) mice, a widely used model of Type 1 diabetes (T1D), which resulted in a diabetes-free state for one year without apparent toxicity and the need to use insulin. cSN50 precipitously reduces the accumulation of islet-destructive autoreactive lymphocytes while enhancing activation-induced cell death of T and B lymphocytes derived from NOD mice. cSN50 attenuated pro-inflammatory cytokine and chemokine production in immune cells in this model of human T1D. cSN50 also provides cytoprotection of beta cells, therefore preserving residual insulin-producing capacity. Because intracellular delivery of a Nuclear Transport Modifier peptide such as cSN50 and cSN50.1 can result in lowering of fasting blood glucose levels and may ameliorate (e.g., reduce, eliminate) insulin resistance, the compositions, methods and cells described herein can also be used for treating Type 2 diabetes (T2D).

14 Claims, 8 Drawing Sheets

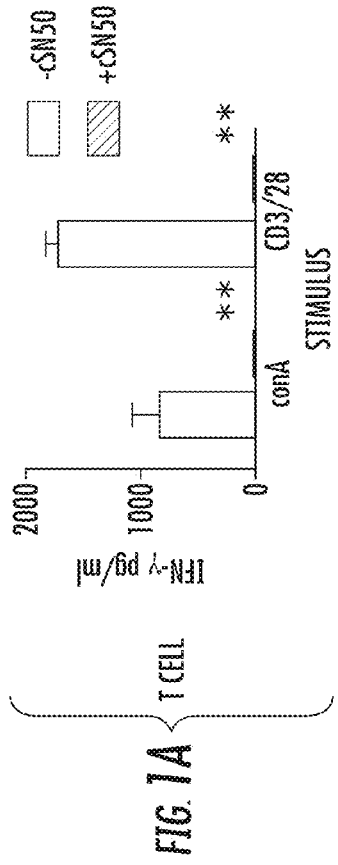
FIG. 1A T CELL
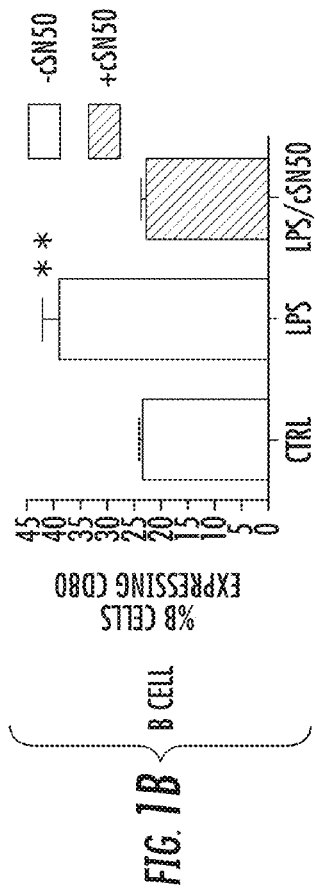
FIG. 1B B CELL
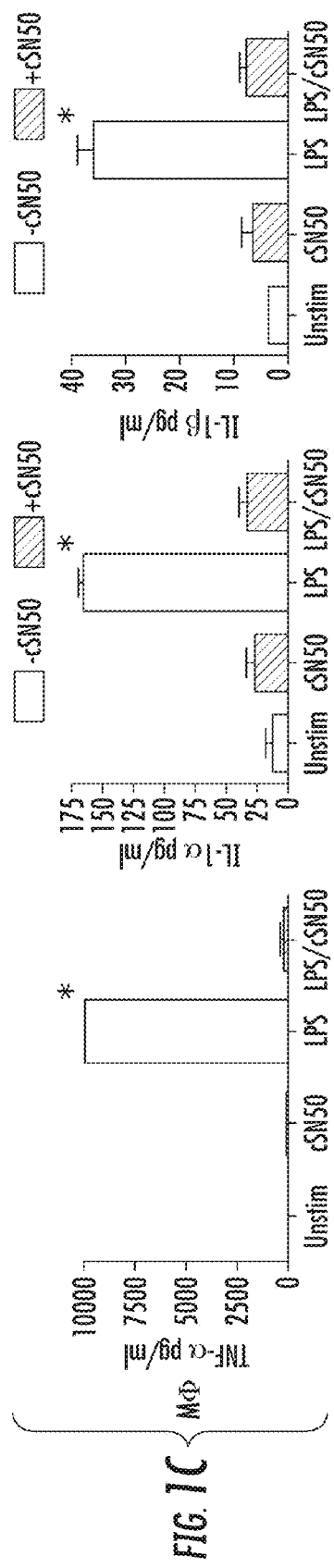
FIG. 1C MΦ

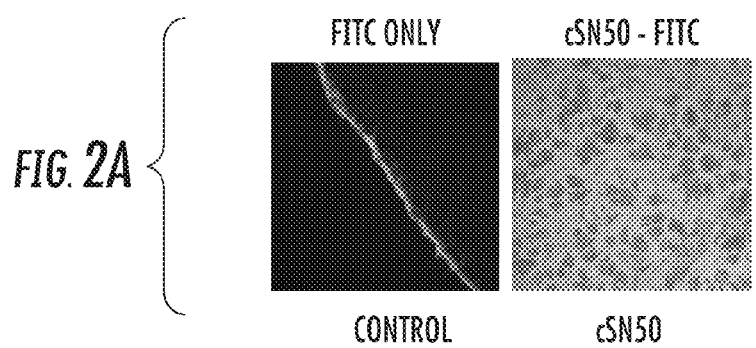
FIG. 2A
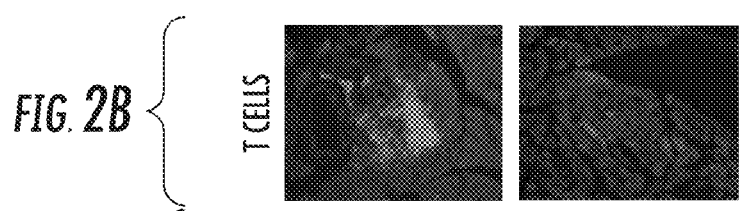
FIG. 2B
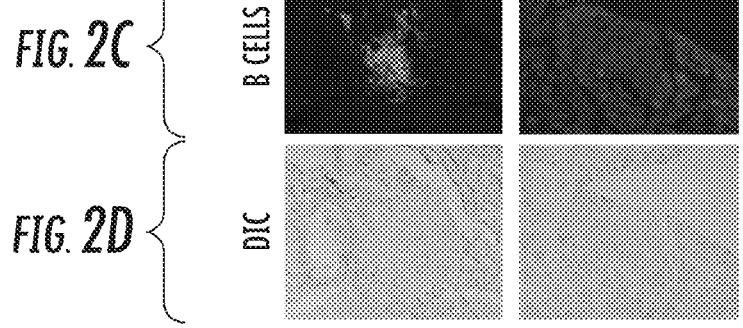
FIG. 2C
FIG. 2D
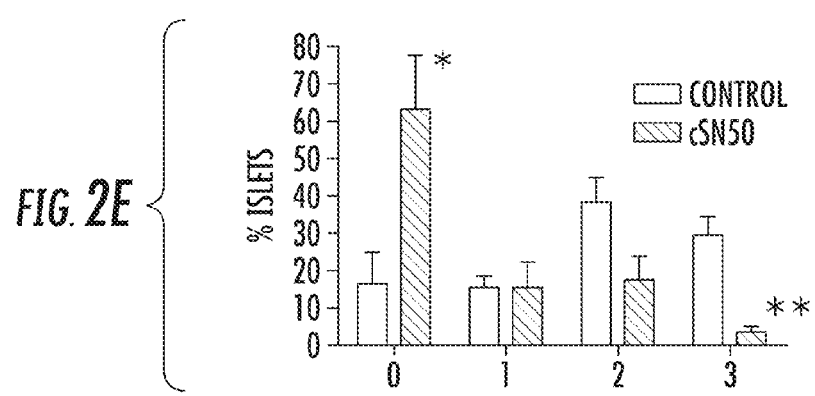
FIG. 2E
FIG. 2F

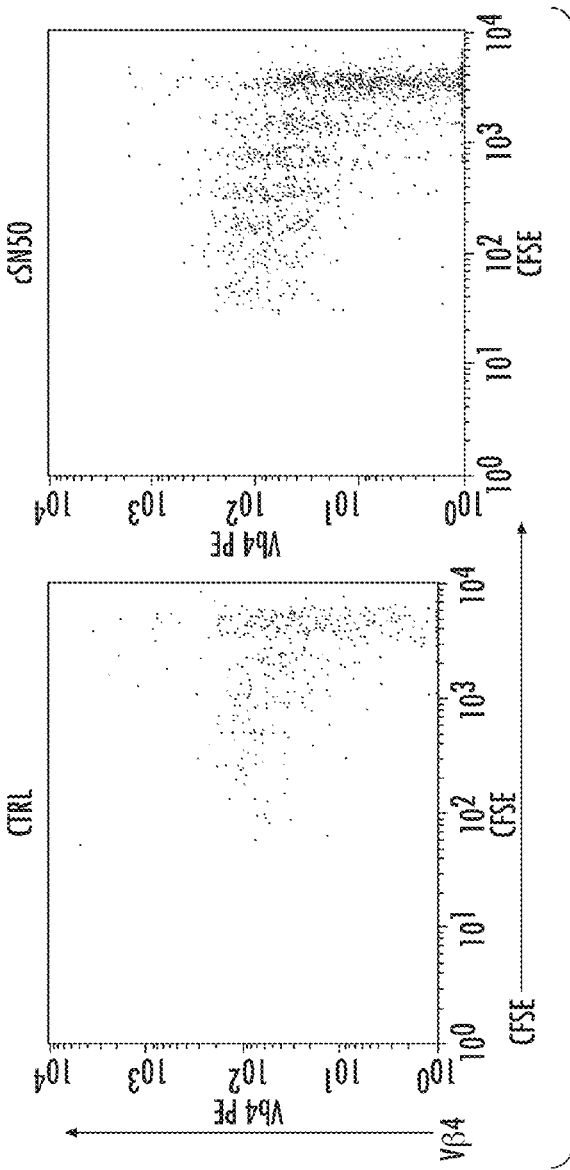
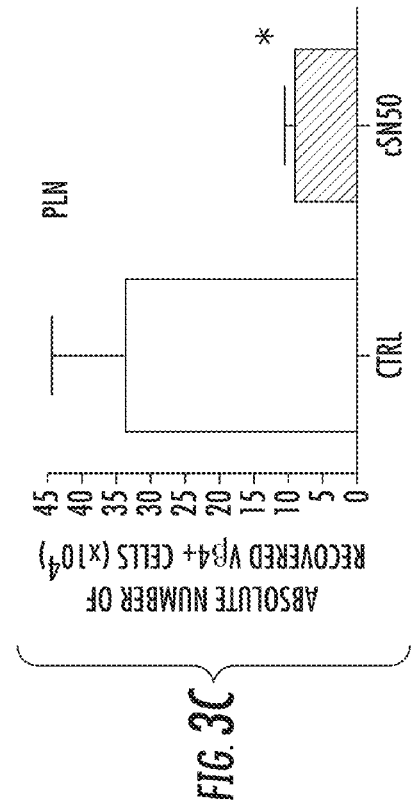
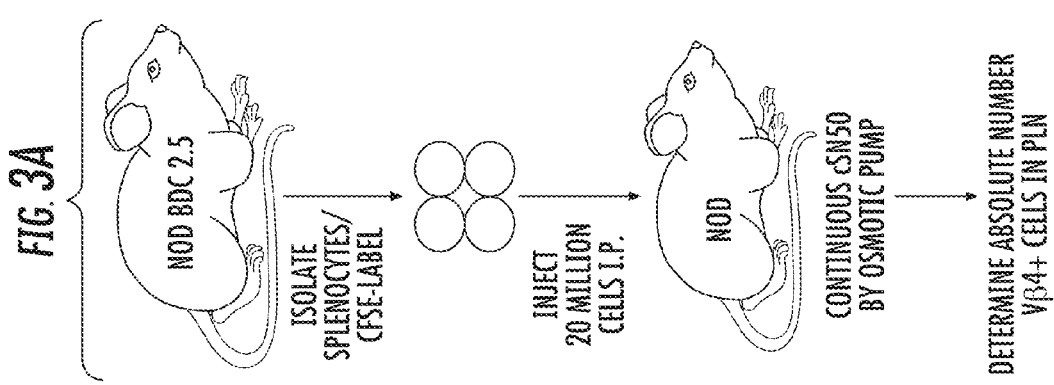
FIG. 3A
FIG. 3B
FIG. 3C

```
                        SEQUENCE LISTING

<160> NUMBER OF SEQ ID NOS: 9

<210> SEQ ID NO 1
<211> LENGTH: 29
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 1

Ala Ala Val Ala Leu Leu Pro Ala Val Leu Leu Ala Leu Leu Ala Pro
1               5                   10                  15

Cys Tyr Val Gln Arg Lys Arg Gln Lys Leu Met Pro Cys
            20                  25

<210> SEQ ID NO 2
<211> LENGTH: 28
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 2

Ala Ala Val Ala Leu Leu Pro Ala Val Leu Leu Ala Leu Leu Ala Pro
1               5                   10                  15

Cys Val Gln Arg Lys Arg Gln Lys Leu Met Pro Cys
            20                  25

<210> SEQ ID NO 3
<211> LENGTH: 29
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: X
<222> LOCATION: (1)..(4)
<223> OTHER INFORMATION: X IS ANY AMINO ACID OR IS ABSENT
<220> FEATURE:
<221> NAME/KEY: X
<222> LOCATION: (8)..(9)
<223> OTHER INFORMATION: X IS ANY AMINO ACID OR IS ABSENT
<220> FEATURE:
<221> NAME/KEY: X
<222> LOCATION: (17)..(19)
<223> OTHER INFORMATION: X IS ANY AMINO ACID OR IS ABSENT
<220> FEATURE:
<221> NAME/KEY: X
<222> LOCATION: (26)..(29)
<223> OTHER INFORMATION: X IS ANY AMINO ACID OR IS ABSENT

<400> SEQUENCE: 3

Xaa Xaa Xaa Xaa Leu Leu Pro Xaa Xaa Leu Leu Ala Leu Leu Ala Pro
1               5                   10                  15

Xaa Xaa Xaa Gln Arg Lys Arg Gln Lys Xaa Xaa Xaa Xaa
            20                  25

<210> SEQ ID NO 4
<211> LENGTH: 29
<212> TYPE: PRT
<213> ORGANISM: ARTIFICIAL SEQUENCE
```

```
<220> FEATURE:
<223> OTHER INFORMATION: SYNTHETIC CONSTRUCT
<220> FEATURE:
<221> NAME/KEY: X
<222> LOCATION: (1)..(4)
<223> OTHER INFORMATION: X IS ANY AMINO ACID OR IS ABSENT
<220> FEATURE:
<221> NAME/KEY: X
<222> LOCATION: (8)..(9)
<223> OTHER INFORMATION: X IS ANY AMINO ACID OR IS ABSENT
<220> FEATURE:
<221> NAME/KEY: X
<222> LOCATION: (18)..(19)
<223> OTHER INFORMATION: X IS ANY AMINO ACID OR IS ABSENT
<220> FEATURE:
<221> NAME/KEY: X
<222> LOCATION: (26)..(28)
<223> OTHER INFORMATION: X IS ANY AMINO ACID OR IS ABSENT

<400> SEQUENCE: 4

Xaa Xaa Xaa Xaa Leu Leu Pro Xaa Xaa Leu Leu Ala Leu Leu Ala Pro
1               5                   10                  15

Cys Xaa Xaa Gln Arg Lys Arg Gln Lys Xaa Xaa Xaa Cys
            20                  25

<210> SEQ ID NO 5
<211> LENGTH: 28
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: X
<222> LOCATION: (1)..(4)
<223> OTHER INFORMATION: X IS ANY AMINO ACID OR IS ABSENT
<220> FEATURE:
<221> NAME/KEY: X
<222> LOCATION: (8)..(9)
<223> OTHER INFORMATION: X IS ANY AMINO ACID OR IS ABSENT
<220> FEATURE:
<221> NAME/KEY: X
<222> LOCATION: (18)..(18)
<223> OTHER INFORMATION: X IS ANY AMINO ACID OR IS ABSENT
<220> FEATURE:
<221> NAME/KEY: X
<222> LOCATION: (25)..(27)
<223> OTHER INFORMATION: X IS ANY AMINO ACID OR IS ABSENT

<400> SEQUENCE: 5

Xaa Xaa Xaa Xaa Leu Leu Pro Xaa Xaa Leu Leu Ala Leu Leu Ala Pro
1               5                   10                  15

Cys Xaa Gln Arg Lys Arg Gln Lys Xaa Xaa Xaa Cys
            20                  25

<210> SEQ ID NO 6
<211> LENGTH: 29
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: X
<222> LOCATION: (1)..(4)
<223> OTHER INFORMATION: X IS ANY AMINO ACID OR IS ABSENT
<220> FEATURE:
<221> NAME/KEY: X
<222> LOCATION: (8)..(9)
<223> OTHER INFORMATION: X IS ANY AMINO ACID OR IS ABSENT
<220> FEATURE:
<221> NAME/KEY: X
<222> LOCATION: (17)..(19)
<223> OTHER INFORMATION: X IS ANY AMINO ACID OR IS ABSENT
<220> FEATURE:
```

-continued

```
<221> NAME/KEY: X
<222> LOCATION: (26)..(29)
<223> OTHER INFORMATION: X IS ANY AMINO ACID OR IS ABSENT

<400> SEQUENCE: 6

Xaa Xaa Xaa Xaa Leu Leu Pro Xaa Xaa Leu Leu Ala Val Leu Ala Pro
1               5                   10                  15

Xaa Xaa Xaa Gln Arg Lys Arg Gln Lys Xaa Xaa Xaa Xaa
            20                  25

<210> SEQ ID NO 7
<211> LENGTH: 28
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

Ala Ala Val Ala Leu Leu Pro Ala Val Leu Leu Ala Val Leu Ala Pro
1               5                   10                  15

Cys Val Gln Arg Lys Arg Gln Lys Leu Met Pro Cys
            20                  25

<210> SEQ ID NO 8
<211> LENGTH: 29
<212> TYPE: PRT
<213> ORGANISM: ARTIFICIAL SEQUENCE
<220> FEATURE:
<223> OTHER INFORMATION: SYNTHETIC CONSTRUCT
<220> FEATURE:
<221> NAME/KEY: X
<222> LOCATION: (1)..(4)
<223> OTHER INFORMATION: X IS ANY AMINO ACID OR IS ABSENT
<220> FEATURE:
<221> NAME/KEY: X
<222> LOCATION: (8)..(9)
<223> OTHER INFORMATION: X IS ANY AMINO ACID OR IS ABSENT
<220> FEATURE:
<221> NAME/KEY: X
<222> LOCATION: (17)..(19)
<223> OTHER INFORMATION: X IS ANY AMINO ACID OR IS ABSENT
<220> FEATURE:
<221> NAME/KEY: X
<222> LOCATION: (26)..(29)
<223> OTHER INFORMATION: X IS ANY AMINO ACID OR IS ABSENT

<400> SEQUENCE: 8

Xaa Xaa Xaa Xaa Leu Leu Pro Xaa Xaa Leu Leu Ala Val Leu Ala Pro
1               5                   10                  15

Xaa Xaa Xaa Gln Arg Asp Glu Gln Lys Xaa Xaa Xaa Xaa
            20                  25

<210> SEQ ID NO 9
<211> LENGTH: 28
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 9

Ala Ala Val Ala Leu Leu Pro Ala Val Leu Leu Ala Val Leu Ala Pro
1               5                   10                  15

Cys Val Gln Arg Asp Glu Gln Lys Leu Met Pro Cys
            20                  25
```

COMPOSITIONS FOR PRESERVING INSULIN-PRODUCING CELLS AND INSULIN PRODUCTION AND TREATING DIABETES

CROSS REFERENCE TO RELATED APPLICATIONS

This application is a continuation-in-part of U.S. nonprovisional application Ser. No. 13/645,754, filed Oct. 5, 2012, which claims priority to U.S. provisional application No. 61/544,018, filed Oct. 6, 2011, both of which are incorporated herein by reference in their entireties.

STATEMENT REGARDING FEDERALLY SPONSORED RESEARCH OR DEVELOPMENT

This invention was made with government support under HL 5 P01 HL068744 awarded by the National Institutes of Health/National Heart, Lung, and Blood Institute and under 1F32DK083161 and 5 K08 DK 090146 awarded by the National Institutes of Health/National Institute of Diabetes, Digestive and Kidney Diseases. The government has certain rights in the invention.

FIELD

The field of the invention is endocrinology, immunology, and cell biology.

BACKGROUND

Insulin-dependent Type 1 diabetes (T1D), also known as Juvenile Diabetes or Insulin-Dependent Diabetes Mellitus, is a devastating autoimmune disease that destroys beta cells within the pancreatic islets and afflicts over 10 million people worldwide. Their autoimmune process is known to lead to hyperlipidemia and accelerated atherosclerosis. These patients face life-long risks for blindness, cardiovascular and renal diseases, and complications of insulin treatment. Increasing evidence regarding the pathomechanism of T1D indicates that islets are destroyed by the relentless attack by autoreactive immune cells evolving from an aberrant action of the innate, in addition to adaptive, immune system that produces islet-toxic cytokines, chemokines, and other effectors of islet inflammation.

T1D results from the progressive destruction of insulin-producing beta cells in pancreatic islets caused by pro-inflammatory and pro-apoptotic effectors of innate and adaptive immunity. Extraordinary advances with insulin monotherapy and understanding of the critical role of the adaptive immune system in the T1D pathomechanism have not translated to diabetes reversal. Patients remain at risk for the serious complications inherent to the autoimmune and metabolic derangements in T1D. Patients with end-stage diabetic nephropathy can receive simultaneous kidney-pancreas (SPK) transplants. Secondly, T1D patients who developed end-stage diabetic nephropathy and received a successful kidney transplant are potentially eligible for pancreas-after-kidney (PAK) transplantation. Thirdly, T1D patients with normal renal function albeit with difficult to control insulin therapy can be treated with pancreas transplant alone (PTA). These approaches have a limited success rates although the positive outcome of SPK and PAK transplants includes decreasing or reversing diabetic neuropathy (Jamiolkowski R M et al. Yale Journal of Biology and Medicine 85 (2012), pp. 37-43). Islet transplantation poses less risk than major organ transplant surgery. However, the risk of immune rejection remains similar. The currently used Edmonton protocol for islet transplantation is continually improving by using the portal vein and liver for implantation of isolated islets. Better preservation of isolated islets before and after transplantation continues to be a challenge that can be met by new treatment that protects transplanted beta cells from autoimmune attack.

Given the side effects of insulin therapy and current immunosuppressive regimens, the search for new therapeutic approaches continues. The requisite roles of islet-specific autoreactive T and B cells have been well established and have been the primary target of current clinical investigations. Building on the role of adaptive immunity, both T cell-directed immunotherapy with anti-CD3 and the B cell-directed action of rituximab (anti-CD20) have shown similar efficacy in delaying the progression of new-onset diabetes. Unfortunately, while clinical benefit to patients in these trials has been recorded (Herold et al. (2005) Diabetes 54: 1763-1769), insulin-secreting capacity continues to decline in treated individuals and these regimens have not restored stable tolerance to islet tissue, perhaps because they do not completely target the islet-destructive autoimmune inflammatory process. New therapies that protect islets from autoimmune destruction and allow continuing insulin production are needed.

BRIEF SUMMARY

Described herein are compositions, methods and kits for preserving the viability of insulin-producing beta cells. As shown in the experiments described herein, a Nuclear Transport Modifier (NTM) in the form of a cell-penetrating cSN50 peptide or cSN50.1 peptide affords in vivo islet protection following a 2-day course of intense treatment in NOD mice, which resulted in a diabetes-free state for one year without apparent toxicity. cSN50 precipitously reduces the accumulation of islet-destructive autoreactive B and T lymphocytes while enhancing activation-induced cell death of T and B lymphocytes derived from autoimmune diabetes-prone, non-obese diabetic (NOD) mice that develop T1D. cSN50 provided attenuation of pro-inflammatory cytokine and chemokine production in immune cells in this model of human T1D. NTM also provides cytoprotection of beta cells, therefore preserving residual insulin-producing capacity before and after transplantation.

Unless otherwise defined, all technical terms used herein have the same meaning as commonly understood by one of ordinary skill in the art to which this invention belongs.

The terms "patient," "subject" and "individual" are used interchangeably herein, and mean an animal (e.g., mammalian (such as human, equine, bovine, ovine, porcine, canine, etc.), reptilian, piscine, etc.) to be treated, diagnosed and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der Waals).

As used herein, the term "insulitis" means a lymphocytic invasion and inflammation of the islets of Langerhans in the pancreas.

By the phrase "nuclear transport modifier" and "NTM" is meant a peptide that is capable of modulating entry of transcription factors into the nucleus. An example of a nuclear transport modifier is a 26-29 amino acid peptide derived from human nuclear factor kappa B1 nuclear localization sequence and from human Fibroblast Growth Factor 4 signal sequence hydrophobic region. This phrase is used interchangeably with the phrase "nuclear import inhibitor."

In an NTM as described herein, any of the amino acid residues in the NTM sequence can be mutated and/or modified (i.e., to form mimetics) so long as the modifications do not affect the translocation-mediating function of the peptide. Thus the word "peptide" includes mimetics and the word "amino acid" includes modified amino acids, unusual amino acids, D-form amino acids, etc.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The term "labeled," with regard to a nucleic acid, protein, probe or antibody, is intended to encompass direct labeling of the nucleic acid, protein, probe or antibody by coupling (i.e., physically or chemically linking) a detectable substance (detectable agent) to the nucleic acid, protein, probe or antibody.

As used herein, the terms "therapeutic," and "therapeutic agent" are used interchangeably, and are meant to encompass any molecule, chemical entity, composition, drug, cell(s), therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, the term "viability" is defined as the ability to live. In the case of insulin-producing beta cells, functional viability of such cells can further include insulin-producing capacity when appropriately stimulated.

Accordingly, described herein is a method of preserving viability of insulin-producing beta cells in pancreatic islets in a mammalian subject including administering a composition including a Nuclear Transport Modifier to the mammalian subject, wherein insulin producing capacity of the insulin-producing beta cells in the pancreatic islets is preserved. The Nuclear Transport Modifier may be, for example, cSN50 having the sequence set forth in SEQ ID NO: 1 or cSN50.1 having the sequence set forth in SEQ ID NO: 2. The composition is typically in an amount sufficient to reduce accumulation of autoreactive lymphocytes in the pancreatic islets and pancreatic lymph nodes and enhance cell death of autoreactive lymphocytes in the pancreatic islets, as well as to enhance expression of at least one anti-inflammatory cytokine (e.g., IL-10) in the pancreatic islets. Administration of the composition decreases autoimmune inflammation by attenuating expression of at least one stress-responsive transcription factor-regulated gene, and autoimmune inflammation-induced apoptosis of the insulin-producing beta cells is decreased or prevented. In the method, sensitivity to activation-induced cell death in T and B lymphocytes that infiltrate pancreatic islets is generally restored. The mammalian subject may be one genetically prone to develop Type 1 diabetes and the composition may be administered to the mammalian subject before detection of hyperglycemia or after detection of hyperglycemia in the subject. Also in the method, the composition can be administered to the mammalian subject at one or more of the following time points: prior to the mammalian subject receiving a transplant of insulin-producing beta cells, concomitant with the mammalian subject receiving a transplant of insulin-producing beta cells, and subsequent to the mammalian subject receiving a transplant of insulin-producing beta cells.

Also described herein is a method of treating diabetes in a mammalian subject including administering a composition including a Nuclear Transport Modifier to the mammalian subject in an amount sufficient for preserving insulin-producing capacity of beta cells in the mammalian subject's pancreas and for at least one of: reducing accumulation of autoreactive lymphocytes in the subject's pancreas; enhancing expression of anti-inflammatory cytokines in the subject's pancreas; and restoring tolerance to pancreatic islets autoantigens. Typically, administration of the composition results in remission of the diabetes in the mammalian subject. The composition may be delivered via any suitable route, e.g., to the mammalian subject's pancreas. The Nuclear Transport Modifier may be, for example, cSN50 having the sequence set forth in SEQ ID NO: 1 or cSN50.1 having the sequence set forth in SEQ ID NO: 2. In one embodiment, the mammalian subject has type 1 diabetes, and the remission occurs in the presence of insulin therapy. In another embodiment, the mammalian subject has type 1 diabetes, and the remission occurs in the absence of insulin therapy. The composition is in an amount sufficient to enhance expression of at least one anti-inflammatory cytokine (e.g., IL-10) in the pancreatic islets. Administration of the composition decreases autoimmune inflammation by attenuating expression of at least one stress-responsive transcription factor-regulated gene, and autoimmune inflammation-induced apoptosis of the insulin-producing beta cells is decreased or prevented. In the method, sensitivity to activation-induced cell death in T and B lymphocytes that infiltrate pancreatic islets is typically restored. The composition may be administered to the mammalian subject at one or more of the following time points: prior to the mammalian subject receiving a transplant of insulin-producing beta cells, concomitant with the mammalian subject receiving a transplant of insulin-producing beta cells, and subsequent to the mammalian subject receiving a transplant of insulin-producing beta cells. In another embodiment of this method of treating diabetes in a mammalian subject, the composition is in an amount sufficient for preserving insulin-producing capacity of beta cells in the mammalian subject's pancreas when administered in combination with insulin and for at least one of: reducing accumulation of autoreactive lymphocytes in the subject's pancreas; enhancing expression of anti-inflammatory cytokines in the subject's pancreas; and restoring tolerance to pancreatic islets autoantigens. In this method, administration of the composition in combination with the insulin results in remission of the diabetes in the mammalian subject.

Further described herein is a method of preserving insulin-producing beta cells including delivering a composition including a Nuclear Transport Modifier to a population of insulin-producing beta cells in an amount sufficient to preserve viability of the insulin-producing beta cells and the insulin-producing capacity of the insulin-producing beta cells if the insulin-producing beta cells are subsequently exposed to proinflammatory stimuli. The Nuclear Transport Modifier may be, for example, cSN50 having the sequence set forth in SEQ ID NO: 1, or cSN50.1 having the sequence set forth in SEQ ID NO: 2. In some embodiments, the population of insulin-producing beta cells is to be transplanted into a mammalian subject in need thereof, and the composition is delivered to the population of insulin-producing beta cells prior to transplantation. In these embodiments, a pancreas including the population of insulin-producing cells may be transplanted into the mammalian subject, and the composition is in an amount sufficient to reduce accumulation of autoreactive lymphocytes in the pancreatic islets and pancreatic lymph nodes and enhance cell death of autoreactive lymphocytes in the pancreatic islets. Typically, the composition is in an amount sufficient to enhance expression of at least one anti-inflammatory cytokine (e.g., IL-10) in the pancreatic islets, and to decrease autoimmune inflammation in the mammalian subject by attenuating expression of at least one stress-responsive transcription factor-regulated gene. Generally, autoimmune inflammation-induced apoptosis of the population of insulin-producing beta cells is decreased or prevented.

Additionally described herein is a method of treating Type 2 diabetes in a mammalian subject. The method includes administering a composition including a Nuclear Transport Modifier to the mammalian subject having Type 2 diabetes in an amount sufficient for lowering blood glucose levels and reducing insulin resistance, wherein administration of the composition results in remission of the Type 2 diabetes in the mammalian subject.

Still further described herein is a composition for treating Type 1 Diabetes in a subject including a pharmaceutically acceptable carrier and a therapeutically effective amount of Nuclear Transport Modifier cSN50.1 having the sequence set forth in SEQ ID NO: 2 sufficient for preserving viability of insulin-producing beta cells and the insulin-producing capacity of the cells in the subject. Insulin-producing cells transduced (e.g., transfected) with the composition or with Nuclear Transport Modifier cSN50.1 having the sequence set forth in SEQ ID NO: 2 are also described herein.

Also described herein is a composition including a pharmaceutically acceptable carrier and a therapeutically effective amount of a Nuclear Transport Modifier including the sequence Xaa Xaa Xaa Xaa Leu Leu Pro Xaa Xaa Leu Leu Ala Leu Leu Ala Pro Xaa Xaa Xaa Gln Arg Lys Arg Gln Lys Xaa Xaa Xaa Xaa (SEQ ID NO: 3), wherein Xaa is any amino acid or is absent. For example, the Nuclear Transport Modifier can have the sequence Xaa Xaa Xaa Xaa Leu Leu Pro Xaa Xaa Leu Leu Ala Leu Leu Ala Pro Cys Xaa Xaa Gln Arg Lys Arg Gln Lys Xaa Xaa Xaa Cys, where Xaa is any amino acid or is absent (SEQ ID NO: 4). As another example, the Nuclear Transport Modifier can have the sequence Xaa Xaa Xaa Xaa Leu Leu Pro Xaa Xaa Leu Leu Ala Leu Leu Ala Pro Cys Xaa Gln Arg Lys Arg Gln Lys Xaa Xaa Xaa Cys, where Xaa is any amino acid or is absent (SEQ ID NO: 5). In one embodiment, the Nuclear Transport Modifier is cSN50.1 having the sequence set forth in SEQ ID NO: 2. In a typical embodiment, the therapeutically effective amount is sufficient for preserving viability of insulin-producing beta cells and insulin-producing capacity of the cells in a subject. In one embodiment, the subject has Diabetes (e.g., Type 1 Diabetes, Type 2 Diabetes), and the therapeutically effective amount is sufficient for treating Diabetes in the subject.

In one example of an NTM, the NTM has the sequence Xaa Xaa Xaa Xaa Leu Leu Pro Xaa Xaa Leu Leu Ala Val Leu Ala Pro Xaa Xaa Xaa Gln Arg Lys Arg Gln Lys Xaa Xaa Xaa Xaa Xaa, where Xaa is any amino acid or is absent (SEQ ID NO: 6). In yet another example, the NTM has the sequence Ala Ala Val Ala Leu Leu Pro Ala Val Leu Leu Ala Val Leu Ala Pro Cys Val Gln Arg Lys Arg Gln Lys Leu Met Pro Cys (SEQ ID NO: 7). In a further example, the NTM has the sequence Xaa Xaa Xaa Xaa Leu Leu Pro Xaa Xaa Leu Leu Ala Val Leu Ala Pro Xaa Xaa Xaa Gln Arg Asp Glu Gln Lys Xaa Xaa Xaa Xaa, where Xaa is any amino acid or is absent (SEQ ID NO: 8). In another example, the NTM has the sequence Ala Ala Val Ala Leu Leu Pro Ala Val Leu Leu Ala Val Leu Ala Pro Cys Val Gln Arg Asp Glu Gln Lys Leu Met Pro Cys (SEQ ID NO: 9).

In a further embodiment, described herein are insulin-producing beta cells (cells that are usually assembled in the pancreatic islets) that include (e.g., are transduced with) a Nuclear Transport Modifier having the sequence Xaa Xaa Xaa Xaa Leu Leu Pro Xaa Xaa Leu Leu Ala Leu Leu Ala Pro Xaa Xaa Xaa Gln Arg Lys Arg Gln Lys Xaa Xaa Xaa Xaa (SEQ ID NO: 3), wherein Xaa is any amino acid or is absent. For example, the Nuclear Transport Modifier can have the sequence Xaa Xaa Xaa Xaa Leu Leu Pro Xaa Xaa Leu Leu Ala Leu Leu Ala Pro Cys Xaa Xaa Gln Arg Lys Arg Gln Lys Xaa Xaa Xaa Cys, where Xaa is any amino acid or is absent (SEQ ID NO: 4). As another example, the Nuclear Transport Modifier can have the sequence Xaa Xaa Xaa Xaa Leu Leu Pro Xaa Xaa Leu Leu Ala Leu Leu Ala Pro Cys Xaa Gln Arg Lys Arg Gln Lys Xaa Xaa Xaa Cys, where Xaa is any amino acid or is absent (SEQ ID NO: 5). The Nuclear Transport Modifier can be, for example, cSN50.1 having the sequence set forth in SEQ ID NO: 2. In a typical embodiment, the Nuclear Transport Modifier is in an amount sufficient for decreasing or preventing autoimmune and/or metabolic inflammation-induced apoptosis of the population of insulin-producing beta cells. The Nuclear Transport Modifier is typically in an amount sufficient for preserving viability of the insulin-producing beta cells and insulin-producing capacity of the insulin-producing beta cells. Such insulin-producing cells can be used for transplantation into a subject in need thereof (e.g., a subject suffering from diabetes). The compositions and methods described herein provide for the preservation of these insulin-producing cells as well as the insulin-producing capacity (e.g., residual insulin-producing capacity) of such cells, before and after transplantation into a subject in need thereof (e.g., a subject suffering from diabetes). These compositions, methods and treated insulin-producing cells thus provide a treatment for diabetes (e.g., Type 1 and Type 2). Additional examples of NTMs include those sequences of SEQ ID NO: 6, SEQ ID NO:7, SEQ ID NO:8 and SEQ ID NO:9.

Although compositions, kits, cells, and methods similar or equivalent to those described herein can be used in the practice or testing of the present invention, suitable compositions, kits, cells, and methods are described below. All publications, patent applications, and patents mentioned herein are incorporated by reference in their entirety. U.S. patent application Ser. No. 14/349,918 ("COMPOSITIONS AND METHODS FOR TREATING AND PREVENTING HYPERLIPIDEMIA, FATTY LIVER, ATHEROSCLEROSIS AND OTHER DISORDERS ASSOCIATED WITH METABOLIC SYNDROME"), and Ser. No. 14/251,135 ("COMPOSITIONS AND METHODS FOR TARGETING NUCLEAR IMPORT SHUTTLES AND TREATING INFLAMMATORY DISORDERS"), and U.S. Pat. No. 7,553,929, for example, are incorporated by reference in their entireties. In the case of conflict, the present specification, including definitions, will control. The particular embodiments discussed below are illustrative only and not intended to be limiting.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-1C show that a Nuclear Transport Modifier suppresses both T Cell Receptor- and Toll-Like Receptor-evoked signaling. Splenocytes from 10 week old NOD females were isolated and stimulated with anti-CD3/CD28 (2 µg/ml), concanavalin (1 µg/ml) (conA), or LPS (5 µg/ml) in the presence or absence of Nuclear Transport Modifier (cSN50 peptide at 30 µM). Supernatants were harvested at 72 h and analyzed. The presence of IFN-γ as a measure of T cell activation using cytokine bead array was analyzed ($p<0.01$ vs. cSN50, t-test) (FIG. 1A). Up-regulation of CD80 (B7.1) as a measure of B cell responsiveness was assessed by flow cytometry ($p<0.01$, Student's t-test) on cells co-expressing CD19 as a B cell marker (FIG. 1B). Pro-inflammatory cytokine production in bone marrow derived-macrophages cultured in L-conditioned media was examined. Differentiated cells were stimulated with LPS (10 ng/ml) in the presence or absence of cSN50 (30 µM). cSN50 inhibited production of TNF-α, IL-1α, and IL-1β (*$p<0.05$, Student's t-test) (FIG. 1C). Data is representative of three or more experiments.

FIGS. 2A-2F show that in vivo intracellular delivery of a Nuclear Transport Modifier to the pancreas attenuates insulitis. To track in vivo delivery of NTM, cSN50 was conjugated to FITC per the manufacturer's instructions. Animals received one i.p. injection of FITC-cSN50 or an amount of FITC of equivalent relative fluorescence. Animals were euthanized after 2 h and 10 µm frozen sections were cut and assessed by confocal microscopy. The cSN50-FITC peptide is distributed throughout the pancreas. In contrast, FITC alone did not penetrate the organ and only the autofluorescent tissue border is seen. Pancreas is shown at 40× magnification (FIG. 2A). cSN50 therapy attenuates ongoing insulitis (FIGS. 2B-2D). 10 week-old NOD females received one injection of cyclophosphamide (Cy, 0.2 mg/g). 45 h after this injection, treatment was begun with cSN50 (35 µg/g every two hours) and continued for 24 h at which time the seven animals in each group (treatment and control) were euthanized and pancreata obtained. Sections were stained for T lymphocytes (FIG. 2B) with anti-CD3-PE (red) and for B lymphocytes (FIG. 2C) with anti-B220 (green). The differential interference contrast (DIC or Nomarski) image is shown in panel (FIG. 2D). Of 7 animals assessed in each group, four NOD mice receiving cSN50 were completely insulitis free as compared to persistent insulitis in all control group animals ($p<0.05$, chi-square). All NOD mice receiving histologic evaluation in cSN50-treated and control groups (n=7 for each) were assigned insulitis scores based on the severity of inflammation (0=no invading cells, 1=peri-insulits, 2=invasive insulitis, 3=minimal residual islet tissue). Comparison of control to cSN50-treated animals shows significantly more unaffected islets in treated mice (*$p<0.05$) and significantly fewer severely affected islets (**$p<0.001$) (FIG. 2E). Three animals were assessed at 1 year follow-up for insulin production and insulitis. Sections were stained with a combination of anti-insulin FITC (green) and a combination of anti-CD3 and anti-B220PE (red) (FIG. 2F). In long-term survivors (right), insulin staining is detected but insulitis was not observed. As a staining control, islets from 15 week old control NODs show significant insulitis.

FIGS. 3A-3C show that autoreactive T cells (BDC2.5 lymphocytes) disappear following in vivo treatment with a Nuclear Transport Modifier. Twenty million CFSE-labeled BDC2.5 splenocytes were transferred to pre-diabetic NOD recipients who received cSN50 peptide or saline by osmotic pump. (FIG. 3A). On day 4 post-transfer, pancreatic lymph node cells were harvested and the proliferation profile of CD4+Thy1.1-cells (FIG. 3B) and absolute number of CFSE+ Vβ4+ cells (FIG. 3C) within the CD4 compartment was determined. Treated mice showed significant reduction in the absolute number of recovered Vβ4+ cells (*$p<0.05$, student's t-test). Figures are representative of three separate experiments.

DETAILED DESCRIPTION

Figure 4A:
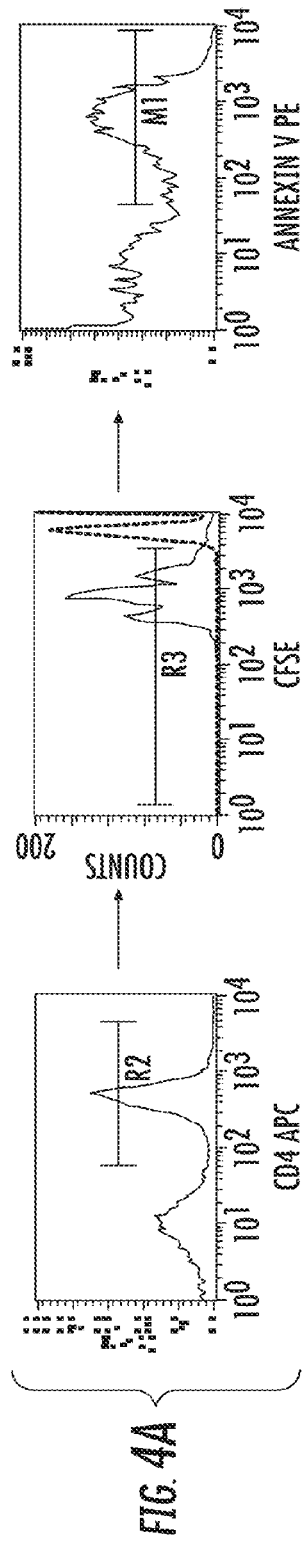
FIGS. 4A-4C show that activation-induced cell death (AICD) is enhanced following ex vivo intracellular delivery of a Nuclear Transport Modifier to splenocytes. Splenocytes from 10 week-old NOD females were labeled with CFSE and stimulated with anti-CD3 (0.05 µg/ml or 2 µg/ml) and anti-CD28 (1 µg/ml) in the presence or absence of cSN50 (30 µM). After 65 h of culture, samples were harvested and labeled with annexin V-PE, anti-CD8 PerCP, and anti-CD4 APC. For analysis of AICD, activation was defined as the achievement of at least one round of division as determined by CFSE-dilution; a representative gating strategy is shown in (FIG. 4A); the undivided peak is highlighted in green and derived from unstimulated cells in the same experiment. The CFSE division history, represented graphically as the number of mitoses per 10,000 CD4 or CD8 T cells, demonstrated no change in proliferation in CD4 or CD8 T cells in the presence of cSN50 (p=NS) (FIG. 4B). Further analysis revealed increased annexin-V staining on activated cells, indicative of cellular apoptosis, for cSN50-treated CD4 and CD8 T cells ($p<0.005$, paired student's t-test) (FIG. 4C). Data is representative of at least 4 separate experiments.

Described herein are compositions, methods, and kits for treating Diabetes (Type 1 and Type 2) and preserving the viability (e.g., functional viability) of insulin-producing beta cells. It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, methods, procedures and components have not been described in detail so as not to obscure the embodiments described herein.

A novel form of immunotherapy that targets nuclear import as described herein can arrest inflammation-driven destruction of insulin-producing beta cells at the site of autoimmune attack within pancreatic islets during the progression of T1D. With respect to T1D progression, pro-inflammatory signaling initiated through stimulation of the principal receptors of innate immunity—Toll-like receptors (TLRs)—is one mechanism that activates antigen-presenting cells (APCs). In turn, these effectors of innate immunity render effector T cells resistant to regulatory T cell (Treg)-mediated suppression. Moreover, autoreactive B cells that recognize insulin and other autoantigens through B cell receptor (BCR) can also escape regulatory mechanism and persist in autoimmune diabetes. As a consequence, loss of peripheral tolerance ensues. This loss is consistent with reports that naïve T cells in NOD mice are resistant to Treg action. Given their escape from both peripheral and central selection processes, autoreactive T and B cells go on to produce critical pro-inflammatory cytokines TNF-α, IL-1β, and IFN-γ that can lead directly to beta cell programmed cell death (apoptosis) (Eizirik D L, and Mandrup-Poulsen T (2001) Diabetologia 44: 2115-2133).

Production of these islet-toxic cytokines depends on tightly-regulated intracellular signal transduction by stress-responsive transcription factors (SRTFs), such as NF-κB, AP-1, NF-AT, STAT-1, and others. NF-κB is the paradigmatic SRTF and has a role in diabetes pathogenesis with crucial roles played at the levels of both lymphocytes and beta cells. However, other SRTFs, including NF-AT, AP-1, and STAT-1, have also been implicated by activating numerous target genes that encode mediators of inflammation and apoptosis, which underlie destruction of islets and other target tissues. These positive effectors of pro-inflammatory immune signaling to the nucleus participate in an auto-stimulatory loop, which amplifies the inflammatory process initiated by microbial and autoimmune triggers. To carry out these potential diabetogenic functions, activated SRTFs are ferried to the nucleus of cells responding to innate and adaptive immune stimulation. Thus, uncontrolled nuclear translocation of SRTFs represents an additional feature of the dysregulated immunity of the murine model of Type 1 Diabetes that may disrupt peripheral tolerance. The genetic ablation of the common TLR adaptor MyD88 protects NOD mice from autoimmune diabetes (Wen L et al 2008 Nature 455:1109-1113). A nuclear transport checkpoint mediated by importins alpha and beta is positioned downstream of MyD88 thereby serving as a common nexus in the innate and adaptive immunity pathways that signal to the nucleus (Hawiger J 2001 Immunol Res 23: 99-109). This culminating step in TLR-evoked innate immunity and BCR- and TCR-evoked adaptive immunity is mediated by nuclear import adaptors known as importins/karyopherins (Hawiger J (2001) Immunol Res 23: 99-109).

Targeting nuclear import of stress-responsive transcription factors evoked by agonist-stimulated innate and adaptive immunity receptors protects islets from autoimmune destruction. The new mode of T1D control disclosed herein allows simultaneous inhibition of TLR-evoked innate immunity and T cell receptor (TCR)-initiated adaptive immunity. A composition and method to target importins/karyopherins by inhibiting nuclear transport offers a new level of control toward dysregulated innate and adaptive immune signaling in T1D. Since both immune responses depend on intracellular signal transduction by SRTFs, the nuclear import mechanism was targeted with a cell-penetrating Nuclear Transport Modifier. Short-term intracellular delivery of this inhibitor (compound) afforded long-term protection of the islets from inflammation-driven apoptosis. This long-lasting (one year) islet-protecting effect, which arrests diabetes progression without the need for insulin therapy, appears to involve the precipitous reduction of autoreactive lymphocytes through enhancement of AICD (activation induced cell death) of T and B lymphocytes. Moreover, this salutary effect of short-term nuclear import targeting is associated with reprogramming of the pro-inflammatory and anti-inflammatory cytokine profile of immune cells isolated from non-obese diabetic (NOD) mice.

The ultimately fatal outcome of autoimmune diabetes in the widely used and clinically relevant murine NOD model of human T1D depends on progressive and relentless destruction of insulin-producing beta cells in pancreatic islets and is inevitable unless insulin-replacement therapy is instituted. Islets are protected from autoimmune attack by intracellular delivery of a Nuclear Transport Modifier peptide such as cSN50 and cSN50.1. These peptides effectively protected islets from immune destruction in the experiments described herein. This protection is vested in significant reduction of islet-reactive T cells, restoration of the sensitivity of autoreactive T and B cells to activation-induced cell death, suppression of islet-toxic pro-inflammatory cytokine production in primary T and B cells and macrophages isolated from NOD mice, and preservation of a key anti-inflammatory cytokine, IL-10. Thus, a Nuclear Transport Modifier extinguished autoimmune inflammation-driven islet loss and prevented further progression of diabetes thereby obviating the need for insulin replacement therapy during a one-year observation period. Because intracellular delivery of a Nuclear Transport Modifier peptide such as cSN50 and cSN50.1 can result in lowering of fasting blood glucose levels and can reduce insulin resistance, the compositions, methods and cells described herein can also be used for treating Type 2 diabetes (T2D).

Nuclear Transport Modifiers include but are not limited to cSN50, cSN50.1, and SN50. Any peptide that is capable of modulating entry into the nucleus of stress-responsive transcription factors (SRTFs) may be a Nuclear Transport Modifier. cSN50 is a fragment-designed cyclic peptide combining the hydrophobic region of the Kaposi fibroblast growth factor signal sequence with the nuclear localization signal (NLS) of the p50-NFκB1 and inserting a cysteine on each side of the NLS to form an intrachain disulfide bond. The amino acid sequence of cSN50 is AAVALLPAVLLALLAP-CYVQRKRQKLMPC (SEQ ID NO: 1). Methods of making and using cSN50 are described, for example, in U.S. Pat. Nos. 7,553,929 and 6,495,518. These patents are incorporated herein by reference in their entireties. In another embodiment, cSN50.1 may be administered to protect islets from immune destruction and preserve viability of insulin-producing beta cells. cSN50.1 is a cyclic peptide having the sequence of cSN50 with the exception that the tyrosine at position 18 of cSN50, adjacent to the first cysteine, has been removed. The amino acid sequence of cSN50.1 is AAVALL-PAVLLALLAPCVQRKRQKLMPC (SEQ ID NO: 2). cSN50.1 was designed to increase the solubility of the cSN50 peptide; i.e., a tyrosine was removed from the sequence of cSN50 to increase solubility. cSN50.1 is also encompassed by SEQ ID NO: 3, SEQ ID NO: 4 and SEQ ID NO: 5. Additional examples of NTMs include fragment-designed and synthesized peptides in which cargo is incorporated as two, rather than one, modules or cargos derived from intracellular proteins other than NFκB1. Such additional examples include the sequences of SEQ ID NO: 6, SEQ ID NO: 7, SEQ ID NO: 8, and SEQ ID NO: 9.

In the experiments described herein, none of the cSN50 peptide-treated animals developed hyperglycemia during the first phase of diabetes onset occurring between days 10-30 after receiving a bolus of cyclophosphamide (Cy), which synchronized the autoimmune diabetes process in NOD mice. In addition to this early protective effect, cSN50 treatment also afforded significant long-term islet protection. While another half of Cy-synchronized control animals progressed to diabetes between days 50 and 100, only two of twenty cSN50-treated animals developed diabetes, a finding suggesting that cSN50 treatment resulted in long-term islet protection in NOD mice that are genetically-prone to T1D. This favorable outcome is supported by the demonstration of in vivo elimination of islet-infiltrating and islet-reactive lymphocytes (FIG. 3), most likely through enhanced AICD, which was demonstrated ex vivo in cSN50 peptide-treated T and B cells derived from diabetes-prone NOD mice (FIG. 4). At higher levels of stimulation (e.g., higher concentrations of the mitogenic stimulus, anti-CD3), the sensitivity to AICD is further increased by the Nuclear Transport Modifier peptide. Thus, even chronic activation of islet-infiltrating T and B cells in autoimmune diabetes that renders NOD mice-derived T and B lymphocytes resistant to AICD may be counteracted by the AICD-enhancing effect of the Nuclear Transport Modifier. This action of NTM may favor rapid elimination of autoreactive and islet-destructive T and B cell clones in NTM-treated NOD mice. The action of cSN50 in a relevant preclinical T1D model adds autoimmune inflammation to the list of conditions in which a Nuclear Transport Modifier has displayed therapeutic utility. Nuclear Transport Modifier delivery and its anti-inflammatory and cytoprotective action are effective in acute inflammation models, including lethal challenge with superantigen, staphylococcal enterotoxin B (SEB), and lipopolysaccharide (LPS), which trigger acute inflammatory lung and liver injury (Liu et al. (2009) Mol Ther 17: 796-802; Liu et al. (2004) J Biol Chem 279: 19239-19246). Moreover, Nuclear Transport Modifiers inhibit nuclear entry of stress-responsive transcription factors, NF-κB, NF-AT, AP-1, and STAT-1 in human T lymphocytes (Hawiger J (1999) Current Opinion in Chem. Biology 3:89-94).

An important aspect of the cSN50 Nuclear Transport Modifier is its ability to reach the pancreas (FIG. 2A) and cells comprising pancreatic lymph nodes, as well as other lymphoid and non-lymphoid organs. The mechanism of intracellular delivery of this peptide has been elucidated and an endocytosis-independent process of crossing the plasma membrane mediated by the membrane-translocating motif (MTM), which is based on the signal sequence hydrophobic region (SSHR) derived from Kaposi FGF, has been documented (Veach et al. (2004) J Biol Chem 279: 11425-11431). The amphipathic helix-based structure of SSHR facilitates its insertion directly into the plasma membrane and the tilted transmembrane orientation permits the translocation of the Nuclear Transport Modifier through the phospholipid bilayer of the plasma membrane directly to the interior of the cell without perturbing membrane integrity. This mechanism explains the efficient delivery of SSHR-guided cargo across the plasma membrane of multiple cell types involved in autoimmune inflammation.

This presents a new avenue for altering the course of diabetes progression as there has been limited success in obviating the need for parenteral insulin-replacement therapy of T1D to date. A broad repertoire of SRTFs-regulated genes that encode mediators of islet inflammation and beta cells apoptosis is attenuated. Contributing to the short-circuiting of this pro-inflammatory signaling cascade, nuclear import modulation reversed resistance of autoreactive T cells to AICD. Indeed, as islet-reactive lymphocytes are likely to be maximally stimulated during disease progression, in the experiments described herein, cSN50 enhanced their deletion as compared to those lymphocytes without islet-reactive specificities (compare FIGS. 2, 3, 5). Thus, cSN50 treatment seems to restore peripheral T and B cell tolerance, which critically depends on the appropriate regulation of lymphocyte AICD in addition to recovery of physiologically immunosuppressive regulatory T cells (Tregs). Tregs are the mainstays of peripheral tolerance. It is surmised that Nuclear Transport Modifier may counteract inhibition of Treg by inflammatory mediators generated in autoimmune disorders such as T1D. This NTM effect is supported by enhanced production of anti-inflammatory cytokine IL-10 linked to Tregs activation (see below).

In addition to enhancing autoreactive lymphocyte elimination, the Nuclear Transport Modifier may also modulate the cytokine milieu established by immune cells in their target organs. cSN50 inhibits pro-inflammatory cytokine expression in ex vivo analyzed NOD splenocytes while preserving and even enhancing the anti-inflammatory cytokine IL-10.

An increase in IL-5 in the plasma of treated mice during the first day of cSN50 therapy was found. Increased levels of IL-4 or IL-13 were not found and thus it is unclear whether this increased IL-5 is indicative of a shift towards a Th2 phenotype. While Th2 shifts have occasionally been associated with diabetes protection, it is not clear that this shift is a part of the true protective mechanism in many cases. The pattern of increased IL-10 and IL-5 was also seen in human subjects in the original trial of anti-CD3 (Herold et al. (2002) N Engl J Med 346: 1692-1698). Cumulatively, these findings suggest that IL-10 and IL-5 may play an important role in modulating the course of Type 1 diabetes in tolerized individuals.

Reduction or complete elimination of islet-destructive autoreactive T and B cells may be useful in treating T1D and potentially other autoimmune diseases. Other autoimmune disorders include Systemic Lupus Erythematosus, Multiple Sclerosis, Rheumatoid Arthritis, Crohn Diseases, and Ulcerative Collitis. Under conditions of metabolic, inflammatory, and oxidant stress, beta cell mass may be further controlled by important interactions between bone marrow-derived cells and islet beta cells. Transcriptional modulation of these interactions via targeting of the nuclear import machinery represents an important new opportunity for therapeutic development. Even though cSN50 can modulate nuclear transport of several stress-responsive transcription factors that utilize importin alpha 1/karyopherin alpha 5 (as well as other importins/karyopherins, e.g., importin alpha 5/karyopherin) for nuclear trafficking, intracellular delivery of the Nuclear Transport Modifier is rapid and restricted to the relatively short intracellular persistence of the injected cargo (Hawiger J., (1999) Current Opinion in Chem. Biology 3:89-94). Despite high intensity dosing of cSN50 in the protocols disclosed herein, short-term or long-term adverse effects were not observed. This suggests that this therapy would be tolerated during longer-term application, if necessary, to prevent or reverse spontaneous disease. In preliminary studies, spontaneous disease was reversed in 40% of the NOD mice during a continuing NTM treatment for 3 weeks. In other disease models, continued cSN50 peptide delivery has been continued for up to 8 weeks without evidence of toxicity including normal animal health and survival, normal weight gain, normal liver enzymes, normal blood cell counts including leukocyte and lymphocyte subsets, and absence of apparent infectious illness.

The data presented herein show that short-term intensive targeting of the nuclear import shuttle for SRTFs can protect islets from relentless autoimmune attack and induce long-term remission of T1D in NOD mice with established insulitis. Chronic inflammatory destruction of beta cells may be reversed without overt signs of toxicity by the intracellular immunotherapy for T1D disclosed herein. Isolated insulin-producing cells may be treated with a Nuclear Transport Modifier or a composition including a Nuclear Transport Modifier to preserve their viability and insulin-producing capacity. Such treated cells can be used for transplantation into a subject in need thereof (e.g., a subject suffering from diabetes). The Nuclear Transport Modifier disarms islet-destroying immune cells and prevents apoptosis of beta cells induced by proinflammatory, autoimmune, and oxidant stress. Intracellular delivery of a Nuclear Transport Modifier to NOD mice protects their insulin-producing beta cells from immune injury and preserves insulin producing capacity. In cultured beta cell lines, activation of cell death executioner caspase 3 following a challenge with proinflammatory and proapoptotic stimuli is attenuated by NTM treatment. Disclosed herein is a new method of preserving residual insulin-producing capacity in Type 1 and Type 2 diabetes, preserving human islets before and after transplantation, and treating diabetes.

Biological and Chemical Methods

Methods involving conventional molecular biology techniques are described herein. Such techniques are generally known in the art and are described in detail in methodology treatises (Sambrook et al. ed., (2001) Molecular Cloning: A Laboratory Manual, 3rd ed., vol. 1-3, Cold Spring Harbor Laboratory Press, Cold Spring Harbor, N.Y.; Ausubel et al. ed., (1992) (with periodic updates) Current Protocols in Molecular Biology, ed., Greene Publishing and Wiley-Interscience, New York).

Compositions for Treating Diabetes in a Subject

Compositions, e.g., pharmaceutical compositions, described herein for treating Type 1 Diabetes in a subject (e.g., a human subject) include a therapeutically effective amount of a Nuclear Transport Modifier (such as cSN50 or cSN50.1) sufficient for preserving viability of insulin-producing beta cells and the insulin-producing capacity of the cells and a pharmaceutically acceptable carrier. Similarly, compositions described herein for treating Type 2 Diabetes in a subject (e.g., a human subject) include a therapeutically effective amount of a Nuclear Transport Modifier (such as cSN50 or cSN50.1) sufficient for lowering blood glucose levels and reducing insulin resistance, and a pharmaceutically acceptable carrier. Such compositions may also include a second therapeutic, e.g., insulin.

In one embodiment, a composition includes a pharmaceutically acceptable carrier and a therapeutically effective amount of an NTM including the sequence Xaa Xaa Xaa Xaa Leu Leu Pro Xaa Xaa Leu Leu Ala Leu Leu Ala Pro Xaa Xaa Xaa Gln Arg Lys Arg Gln Lys Xaa Xaa Xaa Xaa (SEQ ID NO: 3), wherein Xaa is any amino acid or is absent. For example, the NTM can have the sequence Xaa Xaa Xaa Xaa Leu Leu Pro Xaa Xaa Leu Leu Ala Leu Leu Ala Pro Cys Xaa Xaa Gln Arg Lys Arg Gln Lys Xaa Xaa Xaa Cys, where Xaa is any amino acid or is absent (SEQ ID NO: 4). As another example, the NTM can have the sequence Xaa Xaa Xaa Xaa Leu Leu Pro Xaa Xaa Leu Leu Ala Leu Leu Ala Pro Cys Xaa Gln Arg Lys Arg Gln Lys Xaa Xaa Xaa Cys, where Xaa is any amino acid or is absent (SEQ ID NO: 5). In one embodiment, the Nuclear Transport Modifier is cSN50.1 having the sequence set forth in SEQ ID NO: 2. In a typical embodiment, the therapeutically effective amount is sufficient for preserving viability of insulin-producing beta cells and insulin-producing capacity of the cells in a subject. In one embodiment, the subject has Diabetes (e.g., Type 1 Diabetes, Type 2 Diabetes), and the therapeutically effective amount is sufficient for treating Diabetes in the subject.

Additional examples of NTMs include the NTM having the sequence Xaa Xaa Xaa Xaa Leu Leu Pro Xaa Xaa Leu Leu Ala Val Leu Ala Pro Xaa Xaa Xaa Gln Arg Lys Arg Gln Lys Xaa Xaa Xaa Xaa, where Xaa is any amino acid or is absent (SEQ ID NO: 6); the NTM having the sequence Ala Ala Val Ala Leu Leu Pro Ala Val Leu Leu Ala Val Leu Ala Pro Cys Val Gln Arg Lys Arg Gln Lys Leu Met Pro Cys (SEQ ID NO: 7); the NTM having the sequence Xaa Xaa Xaa Xaa Leu Leu Pro Xaa Xaa Leu Leu Ala Val Leu Ala Pro Xaa Xaa Xaa Gln Arg Asp Glu Gln Lys Xaa Xaa Xaa Xaa, where Xaa is any amino acid or is absent (SEQ ID NO: 8); and the NTM having the sequence Ala Ala Val Ala Leu Leu Pro Ala Val Leu Leu Ala Val Leu Ala Pro Cys Val Gln Arg Asp Glu Gln Lys Leu Met Pro Cys (SEQ ID NO: 9).

Method of Preserving Viability of Insulin-Producing Beta Cells in Pancreatic Islets in a Mammalian Subject A typical method of preserving viability of insulin-producing beta cells in pancreatic islets in a mammalian subject includes administering a composition including a Nuclear Transport Modifier to the mammalian subject. In this method, the insulin producing capacity of the insulin-producing beta cells in the pancreatic islets is preserved. Any suitable Nuclear Transport Modifier can be used, e.g., cSN50 having the sequence set forth in SEQ ID NO: 1, cSN50.1 having the sequence set forth in SEQ ID NO: 2, etc. The composition is typically in an amount sufficient to result in one or more of the following: a reduction of accumulation of autoreactive lymphocytes in the pancreatic islets and pancreatic lymph nodes; enhancement of cell death of autoreactive lymphocytes in the pancreatic islets; enhancement of expression of at least one anti-inflammatory cytokine (e.g., IL-10) in the pancreatic islets; a decrease in autoimmune inflammation by attenuating expression of at least one SRTF-regulated gene; reduction or prevention of autoimmune inflammation-induced apoptosis of the insulin-producing beta cells; and restoration of sensitivity to activation-induced cell death in T and B lymphocytes that infiltrate pancreatic islets. In the method, the composition can be administered to the mammalian subject at one or more time points, e.g., prior to diagnosis of T1D in a genetically prone subject (e.g., a subject whose family has a relatively high incidence of T1D), after diagnosis of T1D and initiation of insulin therapy, prior to the subject receiving a transplant of insulin-producing beta cells, concomitant with the subject receiving a transplant of insulin-producing beta cells, and subsequent to the subject receiving a transplant of insulin-producing beta cells.

Method of Treating Type 1 Diabetes in a Subject

The therapeutic methods of the invention in general include administration of a therapeutically effective amount of a composition as described herein to a subject (e.g., animal) in need thereof, including a mammal, particularly a human. Such treatment will be suitably administered to subjects, particularly humans, suffering from, or having, diabetes or signs thereof. The composition may also be added to beta cells to protect their viability before and after transplantation. The compositions herein may also be used in the treatment of any other disorders in which inflammation-driven destruction of beta cells may be implicated.

In a typical method of treating Type 1 diabetes in a mammalian subject, the method includes administering a composition including a Nuclear Transport Modifier (e.g., cSN50, cSN50.1) to the mammalian subject in an amount sufficient for preserving insulin-producing capacity of beta cells in the mammalian subject's pancreas and for at least one of: reducing accumulation of autoreactive lymphocytes in the subject's pancreas; enhancing expression of anti-inflammatory cytokines in the subject's pancreas; and restoring tolerance to pancreatic islets autoantigens. Administration of the composition results in remission of the diabetes in the mammalian subject. In some embodiments, the composition is delivered to the mammalian subject's pancreas. In one embodiment, the mammalian subject has Type 1 diabetes, and the remission occurs in the absence of insulin therapy. In another embodiment, the mammalian subject has Type 2 diabetes, and receives insulin therapy in combination with a composition as described herein. In this embodiment, the remission occurs in the presence of insulin therapy. In the methods described herein, a composition as described herein may also include insulin, and thus the Nuclear Transport Modifier and insulin are administered to the subject as one composition. Alternatively, insulin may be administered to the subject separately from the composition including a Nuclear Transport Modifier, either at the same time (concomitantly) or at different time points. Insulin and compositions including insulin can be administered by any suitable route. Methods of delivering insulin are well known in the art.

For treating diabetes, the compositions described herein can be administered at any appropriate time point. For example, a composition may be administered before, during and after a transplantation (e.g., islet transplantation, pancreas transplantation). In one embodiment, a composition is administered before and after transplantation (e.g., of a pancreas or islets), thereby suppressing an immune attack on the transplanted organ or cells and prolonging their lifespan. As additional examples, a composition may be administered to a subject (e.g., a human patient) known to be genetically prone to T1D and before hyperglycemia (diabetes) is apparent, after hyperglycemia is first detected, and when hyperglycemia is well established (this means that all pancreatic islets are destroyed). At the time when hyperglycemia is well established, a patient may be a candidate for pancreas or islet transplantation and administration of the compositions described herein and employment of the methods described herein should "prime" the patient for pancreas or islet transplantation. Thereafter, such treatment should continue to protect a transplanted pancreas or islets from beta cell-directed injury. In some embodiments, use of the compositions, cells and methods described herein may promote or enable transplantation by reducing autoreactive B and T cells in a patient before receipt of the organ or islets (to be transplanted), i.e., suppressing an immune attack on the transplanted organ or islets, thereby preserving transplanted cell (e.g., islet cells) viability by shielding them from autoreactive B and T lymphocytes.

In some embodiments, a subject's response to the compositions described herein (and optionally to insulin therapy as well) is measured. In one embodiment, the invention provides a method of monitoring treatment progress. The method includes the step of determining a level of expression of diagnostic markers such as blood glucose, C-peptide, anti-insulin antibody, IFN-γ, TNF-α, IL-1α, IL-1β, and IL-10 (e.g., any target delineated herein modulated by a composition or agent described herein, a protein or indicator thereof, etc., or diagnostic measurement (e.g., screen, assay)) in a subject suffering from or susceptible to a disorder or symptoms thereof associated with Type 1 Diabetes in which the subject has been administered a therapeutic amount of a composition as described herein for treating the disease or symptoms thereof. The level of marker determined in the method can be compared to known levels of marker in either healthy normal controls or in other afflicted patients to establish the subject's disease status. In preferred embodiments, a second level of marker (e.g., C-peptide, anti-insulin antibody, IFN-γ, TNF-α, IL-1α, and IL-1β, and IL-10) in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Also described herein are diagnostic and theranostic methods useful to determine whether the subject or beta cells are susceptible to the treatment methods of the invention. The term "theranostics" generally refers to therapy-specific diagnostics, which is the use of diagnostic testing to diagnose the disease, choose the correct treatment regime for that disease, and monitor the patient response to therapy. Theranostic tests can be used to predict and assess drug response in individual patients, and are designed to improve drug efficacy by selecting patients for treatments that are particularly likely to benefit from the treatments. Theranostic tests are also designed to improve drug safety by identifying patients that may suffer adverse side effects from the treatment.

Method of Treating Type 2 Diabetes in a Subject

In some embodiments, the methods described herein are used to treat subjects susceptible to or suffering from Type 2 diabetes. In such embodiments, not only are beta cells protected from metabolic insults e.g. glucotoxicity, but insulin resistance may be reduced. Intracellular delivery of a Nuclear Transport Modifier peptide such as cSN50 and cSN50.1 can result in lowering of blood glucose levels and may reduce insulin resistance. In a typical method of treating Type 2 diabetes in a mammalian subject, the method includes administering a composition including a Nuclear Transport Modifier (e.g., cSN50, cSN50.1) to the mammalian subject in an amount sufficient for lowering blood glucose levels and reducing insulin resistance, and a pharmaceutically acceptable carrier. In a subject suffering from Type 2 diabetes, administration of the composition results in remission of the diabetes in the mammalian subject.

Kits

Described herein are kits for treating Type 1 diabetes in a subject and protecting beta cells (in vitro, in vivo, ex vivo, in pancreatic islets). Such a kit may be particularly useful for preserving beta cell viability and function of such cells before and after transplantation. In one embodiment, a kit includes: a composition including a pharmaceutically acceptable carrier, a Nuclear Transport Modifier such as cSN50 or cSN50.1, packaging, and instructions for use. In the composition, the amount of Nuclear Transport Modifier such as cSN50 or cSN50.1 is sufficient for treating Type 1 Diabetes or preserving the viability and function of beta cells in pancreatic islets. In another embodiment, a kit includes beta cells which have been treated with a composition as described herein. Also described herein are kits treating Type 2 diabetes. In such an embodiment, a kit can include a pharmaceutically acceptable carrier, packaging, instructions for use, and a Nuclear Transport Modifier (e.g., cSN50, cSN50.1) in an amount sufficient for lowering blood glucose levels and reducing insulin resistance. Optionally, kits may also contain one or more of the following: containers which include positive controls, containers which include negative controls, photographs or images of representative examples of positive results and photographs or images of representative examples of negative results.

Administration of Compositions and Cells

The administration of a composition (e.g., a pharmaceutical composition) including a Nuclear Transport Modifier such as cSN50 or cSN50.1 in an amount effective for, for example, treating Type 1 Diabetes in a subject and protecting beta cells before and after transplantation, may be by any suitable means that results in a concentration of the therapeutic that is effective. cSN50 or cSN50.1 may be contained in any appropriate amount in any suitable carrier substance, and are generally present in an amount of 1-95% by weight of the total weight of the composition. The composition may be provided in a dosage form that is suitable for local or systemic administration (e.g., parenteral, subcutaneously, intravenously, intramuscularly, or intraperitoneally, intrahepatically). The pharmaceutical compositions may be formulated according to conventional pharmaceutical practice (see, e.g., Gennaro, A. R. ed. (2000) Remington: The Science and Practice of Pharmacy (20th ed.), Lippincott Williams & Wilkins, Baltimore, Md.; Swarbrick, J. and Boylan, J. C., eds. (1988-1999) Encyclopedia of Pharmaceutical Technology, Marcel Dekker, New York).

Compositions as described herein may be administered parenterally by injection, infusion or implantation (subcutaneous, intravenous, intramuscular, intraperitoneal, intrahepatic, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in, for example, Gennaro, A. R. supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that treats Type 1 Diabetes and protects beta cells (e.g., before and after transplantation), and that treats Type 2 Diabetes and lowers blood glucose levels, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly (caprolactone), poly(lactic acid), poly(glycolic acid) or poly (ortho esters) or combinations thereof).

Formulations for oral use include tablets containing the active ingredient(s) (e.g., cSN50 or cSN50.1) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Swarbrick, J. and Boylan, J. C., supra. At least two therapeutics (e.g., a composition including cSN50 or cSN50.1, as well as a second anti-Type 1 Diabetes or islet transplantation therapeutic or anti-Type 2 Diabetes therapeutic) may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment. Compositions as described herein can also be formulated for inhalation and topical applications. Optionally, an anti-diabetes or transplantation therapeutic may be administered in combination with any other standard anti-diabetes or transplantation therapy; such methods are known to the skilled artisan (see, e.g., Gennaro, supra). Combinations are expected to be advantageously synergistic. Therapeutic combinations that preserve viability of insulin-producing beta cells are identified as useful in the compositions and methods described herein.

In ex vivo methods of preserving insulin-producing beta cells in the islets prepared for transplantation and treating diabetes, islets treated with a composition as described herein can be delivered (e.g., transplanted) to a subject via any suitable means. One or more of the delivery means described herein for administering compositions can be used for delivery of treated islets to a subject. In a typical embodiment of islet transplantation, the currently used Edmonton protocol (see, e.g., N Engl J Med 2006; 355:1318-1330) involving use of the portal vein and liver for implantation of isolated islets may be used. However, any suitable method of islet transplantation may be used. Islets may be obtained from any suitable source. For example, two to four whole pancreases from human donors may be used for a single islet cell transplant implanted in the recipient's liver.

The therapeutic methods described herein in general include administration of a therapeutically effective amount of the compositions and/or cells (e.g., islets, pancreas) described herein to a subject (e.g., animal) in need thereof, including a mammal, particularly a human. Such treatment will be suitably administered to subjects, particularly humans, suffering from, having, susceptible to, or at risk for Type 1 Diabetes or beta cell destruction or at risk for Type 2 Diabetes and insulin resistance and elevated glucose levels. Determination of those subjects "at risk" can be made by any objective or subjective determination by a diagnostic test or opinion of a subject or health care provider. The methods, cells, and compositions herein may be also used in the treatment of any disorders in which inflammation-driven destruction of cells may be implicated.

An example of cells that can be administered as described herein includes insulin-producing beta cells (cells that are usually assembled in the pancreatic islets) that include (e.g., are transduced with) an NTM having the sequence Xaa Xaa Xaa Xaa Leu Leu Pro Xaa Xaa Leu Leu Ala Leu Leu Ala Pro Xaa Xaa Xaa Gln Arg Lys Arg Gln Lys Xaa Xaa Xaa Xaa (SEQ ID NO: 3), wherein Xaa is any amino acid or is absent. For example, the NTM can have the sequence Xaa Xaa Xaa Xaa Leu Leu Pro Xaa Xaa Leu Leu Ala Leu Leu Ala Pro Cys Xaa Xaa Gln Arg Lys Arg Gln Lys Xaa Xaa Xaa Cys, where Xaa is any amino acid or is absent (SEQ ID NO: 4). As another example, the NTM can have the sequence Xaa Xaa Xaa Xaa Leu Leu Pro Xaa Xaa Leu Leu Ala Leu Leu Ala Pro Cys Xaa Gln Arg Lys Arg Gln Lys Xaa Xaa Xaa Cys, where Xaa is any amino acid or is absent (SEQ ID NO: 5). The NTM can be, for example, cSN50.1 having the sequence set forth in SEQ ID NO: 2. In a typical embodiment, the NTM is in an amount sufficient for decreasing or preventing autoimmune and/or metabolic inflammation-induced apoptosis of the population of insulin-producing beta cells. The NTM is typically in an amount sufficient for preserving viability of the insulin-producing beta cells and insulin-producing capacity of the insulin-producing beta cells. Such insulin-producing cells can be used for transplantation into a subject in need thereof (e.g., a subject suffering from diabetes). The compositions and methods described herein provide for the preservation of these insulin-producing cells as well as the insulin-producing capacity (e.g., residual insulin-producing capacity) of such cells, before and after transplantation into a subject in need thereof (e.g., a subject suffering from diabetes). These compositions, methods and treated insulin-producing cells thus provide a treatment for diabetes (e.g., Type 1 and Type 2).

Additional examples of NTMs include the NTM having the sequence Xaa Xaa Xaa Xaa Leu Leu Pro Xaa Xaa Leu Leu Ala Val Leu Ala Pro Xaa Xaa Xaa Gln Arg Lys Arg Gln Lys Xaa Xaa Xaa Xaa, where Xaa is any amino acid or is absent (SEQ ID NO: 6); the NTM having the sequence Ala Ala Val Ala Leu Leu Pro Ala Val Leu Leu Ala Val Leu Ala Pro Cys Val Gln Arg Lys Arg Gln Lys Leu Met Pro Cys (SEQ ID NO: 7); the NTM having the sequence Xaa Xaa Xaa Xaa Leu Leu Pro Xaa Xaa Leu Leu Ala Val Leu Ala Pro Xaa Xaa Xaa Gln Arg Asp Glu Gln Lys Xaa Xaa Xaa Xaa, where Xaa is any amino acid or is absent (SEQ ID NO: 8); and the NTM having the sequence Ala Ala Val Ala Leu Leu Pro Ala Val Leu Leu Ala Val Leu Ala Pro Cys Val Gln Arg Asp Glu Gln Lys Leu Met Pro Cys, where Xaa is any amino acid or is absent (SEQ ID NO: 9).

Effective Doses

The compositions (e.g., pharmaceutical compositions) and cells (e.g., islets, pancreas) described herein are preferably administered to an animal (e.g., mammalian (such as human), reptilian, piscine, etc.) in an effective amount, that is, an amount capable of producing a desirable result in a treated animal (e.g., preserving viability of insulin-producing beta cells, treating diabetes, lowering blood glucose levels, reducing insulin resistance). Such a therapeutically effective amount can be determined according to standard methods. Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently.

EXAMPLES

The following examples are included to demonstrate preferred embodiments of the present disclosure. It should be appreciated by those of skill in the art that the techniques disclosed in the examples which follow represent techniques discovered by the inventors to function well and thus can be considered to constitute preferred modes for its practice. However, those of skill in the art should, in light of the present disclosure, appreciate that many changes can be made in the specific embodiments which are disclosed and still obtain a like or similar result without departing from the spirit or scope of the disclosure. The following Examples are offered by way of illustration and not by way of limitation.

Example 1

Mice and Diabetes Monitoring

NOD/LtJ, NOD-BDC2.5 and C57BL/6 mice were purchased from the Jackson Laboratories (Bar Harbor, Me.) at 6-8 weeks of age. All mice were housed and maintained according to the guidelines for use and care of laboratory animals as set forth by Vanderbilt University and regulated via the Vanderbilt IACUC. All NOD mice were monitored twice weekly for the development of diabetes by blood glucose measurement with FreeStyle® FastTake test strips (Abbott Laboratories, Abbott Park, Ill.). Two consecutive glucose measurements >220 mg/dl constituted a diagnosis of diabetes. A colony of NOD mice kept by a collaborating laboratory in the same animal suite has a spontaneous diabetes incidence of 80-90% in females by 30 weeks of age indicating an animal environment that is conducive for diabetes development.

Isolation of Lymphoid Cells and Preparation of Bone Marrow Derived Macrophages

Splenocytes and lymph node cells were prepared by dispersion of the organ and passage through a 70-μm cell strainer followed by red cell lysis and resuspension in the media of choice for the given experiment. For preparation of primary macrophages, bone marrow from pre-diabetic, 8-12 week old female NOD mice was prepared by flushing mouse femurs and tibias with ice-cold DMEM supplemented with L-glutamine. Bone marrow cells were pooled, passed through a 25⅝-gauge needle, and filtered through a 70-μm cell strainer. Pooled cells ($1 \times 10^6$ cells/ml) were suspended in DMEM supplemented with 10% FBS, 10 mM HEPES, penicillin (100 U/ml), streptomycin (100 μg/ml), and 20% L929 conditioned medium followed by plating on 150-mm bacterial Petri dishes. Cells were incubated at 37° C. in 5% $CO_2$ in humid air. Every 3 days, non-adherent cells were removed, cells were washed, and culture medium was replaced. Cells were used in experiments after 10 days of culture for up to 2 weeks after maturation. When analyzed by flow cytometry, 95% of the adherent cells were MAC3+, CD3−, and B220−. The viability of BMDMs was >80% before use in all experiments.

Ex Vivo Stimulation of NOD Lymphocytes

Cells were plated in 24-well plates at a density of $1 \times 10^6$ total cells/ml in DMEM containing 10% HI-FCS, penicillin (100 U/ml), streptomycin (100 μg/ml), 2-mercaptoethanol (55 μM), and varying amounts of the identified stimulus including anti-CD3 (0-2 μg/ml) with 1 μg/ml anti-CD28, LPS (5 μg/ml), or concanavalin A (1 μg/ml) (conA). All cells were incubated for 65-70 h at 37° C. in 5% $CO_2$.

Synthesis, Purification, and Labeling of a Cell-Penetrating Peptide Inhibitor of Nuclear Import (cSN50) and its Non-Cell-Penetrating Control (cN50)

Cell-penetrating peptide (cSN50, MW=3149; cSN50.1, MW=2986), and non-cell-penetrating peptide (cN50, MW=1651), were synthesized, purified, filter-sterilized, and analyzed as described elsewhere (Torgerson et al. (1998) J Immunol 161: 6084-6092; Liu et al. (2000) J Biol Chem 275: 16774-16778). To monitor the intracellular delivery of peptides to pancreas, cSN50 peptide was coupled with fluorescein isothiocyanate (FITC, Pierce) according to the manufacturer's protocol.

In Vivo Intracellular Peptide Delivery to the Pancreas

For in vivo detection of fluorescein-labeled peptides in the pancreas, NOD mice were sacrificed at 2 h after intraperitoneal (i.p.) injection of 0.7 mg of FITC-labeled cSN50 peptide/mouse. The pancreata were washed with saline and prepared for cryosections (10 μm thickness). Control solution of FITC alone with equivalent fluorescence units was injected separately to track distribution to the pancreas.

Synchronization of T1D Progression with Cyclophosphamide

At 10-11 weeks of age, female NOD mice received an intraperitoneal bolus injection of 200 mg/kg cyclophosphamide (Sigma). Cyclophosphamide was prepared by reconstitution of powder in sterile saline for injection.

Treatment with Nuclear Transport Modifier and Control 45 h after diabetes synchronization with cyclophosphamide, treatment with cSN50 or control was initiated. Mice receiving cSN50 were given 35 μg/g of cSN50 i.p. every two hours for the next 48 h. Control mice received either saline or non-cell penetrating cN50 peptide at molar equivalent (20 μg/g). cN50 peptide, contains the cyclized NLS but lacks the membrane translocating motif. All injections were delivered in a volume of 100 μl of sterile saline Immunohistochemistry Freshly harvested pancreata were fixed in 4% paraformaldehyde-0.1 M PBS (12.07 g of $Na_2HPO_4$ (dibasic), 2.04 g of $KH_2PO_4$ (monobasic), 8.0 g of NaCl, 2.0 g of KCl; pH 7.5, same-day preparation) for 1.5 h at 4° C. under mild agitation, followed by four washings in 0.1 M PBS over a period of 2 h at 4° C. under mild agitation. Tissue was equilibrated in 30% sucrose in 1×PBS (Invitrogen) overnight at 4° C. until tissue settled to the bottom of the tube. Pancreata were then frozen in OCT (Sakura Finetek), and cut into 8 μm sections using a cryostat microtome (Leica). Sections were rehydrated with PBS for 2 min before blocking for 30 min at room temperature in blocking buffer (5% normal goat serum and 1% BSA in 1×PBS), then stained with anti-B220-FITC and anti-CD3 PE for 1 h at room temperature, washed with PBS, and mounted in fluorescent mounting medium (Dako). Slides were examined by conventional fluorescence microscopy using an Olympus BX60 epifluorescence microscope. Images were captured using a charge-coupled device camera and MagnaFire software (Optronics) and optimized for signal-to-noise using Adobe Photoshop software (Adobe Systems). A pancreas was deemed insulitis-free if at least 40 islets were identified and no islet had evidence of T or B-cell staining.

Flow Cytometry

One million splenocytes were suspended in PBS containing 0.1% azide and 3% FCS and surface stained with the following mAbs: RM4-5 (anti-CD4), 1D3 (anti-CD19), RA3-6B2 (anti-B220), 53-6.7 (anti-CD8), or 16-10A1 (anti-CD80), each conjugated to FITC, PE, PE-Cy7, Cychrome or APC as appropriate. Annexin V staining was performed in the appropriate binding buffer as supplied. All reagents were obtained from BD Pharmingen (San Jose, Calif.). All samples were analyzed on FACSCalibur flow cytometer (Becton Dickinson, Mountain View, Calif.) using CellQuest software.

CFSE Labeling

Spleens were harvested, and cells were labeled and prepared. Mitotic events were determined based on the two-fold decrease in fluorescence intensity with each division of labeled cells.

In Vivo Tracking of Islet-Reactive CD4 T Cell Elimination During Nuclear Transport Modifier Treatment Splenocytes were isolated from NOD BDC2.5 TCR transgenic mice and labeled with CFSE. A total of $20 \times 10^6$ of these CFSE-labeled cells was injected intraperitoneally into NOD-Thy1.1 mice. For BDC2.5 T cell transfers, optimal activation occurs at about 90 h, and so recipient cells were harvested at this time point from pancreatic lymph nodes. Single cell suspensions were prepared and stained with anti-Thy-1.1 PE-Cy7 (OX-7), anti-TCR Vβ4-PE (the BDC2.5 transgene utilizes Vβ4 TCR) and anti-CD4 APC (RM4-5) to allow for the identification of the transferred CD4 T cells using flow cytometry. To allow continuous and facile peptide delivery throughout the 4-day incubation period, mice were implanted with osmotic pumps the day prior to cell transfer. Implantation was achieved following induction of anesthesia with ketamine and xylazine per standard protocol and the pump was placed into a subscapular location. The wound was closed with a single staple. These 4-day pumps deliver 100 μl of fluid at 1 μl/hr and generally begin infusion about 12 hrs after implantation (Alzet, Cupertino, Calif.).

Cytokine Detection by Cytokine Bead Array

Serum or plasma samples were obtained daily by saphenous vein bleeding. Other samples for cytokine determination were obtained from supernatants of stimulated lymphocyte cultures. Cytokine concentration was determined by cytokine bead array and comparison to a standard curve (BD Biosciences, San Jose, Calif.) or with the MILLIPLEX mouse cytokine-chemokine kit (Millipore, St. Charles, Mo.) according to the manufacturer's specifications.

Clinical Chemistry

ALT and BUN levels were determined on a VITROS 250 Chemistry analyzer using multi-layered vitros slides and colorimetric or enzyme rate tests as appropriate.

Statistical Analysis

Statistical comparison between groups was performed by log-rank analysis, Student's t-test or ANOVA as appropriate. A p-value less than 0.05 was considered significant.

Example 2

Primary lymphocytes and macrophages from NOD mice are susceptible to attenuation of T cell receptor (TCR)- and Toll-like receptor (TLR)-evoked pro-inflammatory signaling, respectively, by a Nuclear Transport Modifier. NOD mice, a widely used model of human T1D, demonstrate genetic predisposition toward autoimmune diabetes as evidenced by numerous immunologic abnormalities of innate and adaptive immunity as compared to normal strains of mice. The Nuclear Transport Modifier, cSN50 peptide, attenuates TCR- and TLR-evoked cytokine/chemokine production in murine models of acute inflammation and apoptosis using normal C57BL/6 and BALB/c strains (Lin et al (1995) Inhibition of nuclear translocation of transcription factor NF-kappa B by a synthetic peptide containing a cell membrane-permeable motif and nuclear localization sequence. J Biol Chem 270: 14255-14258; Hawiger J (1999) Current Opinion in Chem. Biology 3:89-94; Liu et al. (2000) J Biol Chem 275: 16774-16778; Liu et al. (2004) J Biol Chem 279: 48434-48442). Therefore, it was examined whether agonist-stimulated T and B lymphocytes and macrophages derived from autoimmune diabetes-prone NOD mice are suppressed by targeting nuclear import with cell-penetrating cSN50 peptide (FIGS. 1A-1C).

The Nuclear Transport Modifier cSN50 suppresses both T Cell Receptor- and Toll-Like Receptor-evoked signaling. Splenocytes from 10 week old NOD females were isolated and stimulated with anti-CD3/CD28 (2 μg/ml), concanavalin (1 μg/ml) (conA), or LPS (5 μg/ml) in the presence or absence of Nuclear Transport Modifier (cSN50 peptide at 30 μM). Supernatants were harvested at 72 h and analyzed. The presence of IFN-γ as a measure of T cell activation using cytokine bead array was analyzed (p<0.01 vs. cSN50, t-test) (FIG. 1A). Up-regulation of CD80 (B7.1) as a measure of B cell responsiveness was assessed by flow cytometry (p<0.01, Student's t-test) on cells co-expressing CD19 as a B cell marker. (FIG. 1B). Pro-inflammatory cytokine production in bone marrow derived-macrophages cultured in L-conditioned media was examined. Differentiated cells were stimulated with LPS (10 ng/ml) in the presence or absence of cSN50 (30 μM). (FIG. 1C). cSN50 inhibited production of TNF-α, IL-1α, and IL-1β (*p<0.05, Student's t-test). Data is representative of three or more experiments.

Isolated NOD splenocytes were stimulated with the T cell agonists anti-CD3/CD28 or concanavalin A (Con A) in the presence or absence of the Nuclear Transport Modifier peptide cSN50 and were measured for the production of the pro-apoptotic cytokine IFN-γ. cSN50 suppressed the robust production of this islet-toxic cytokine (FIG. 1A).

The effect of cSN50 on B cells and bone marrow-derived macrophages (BMDM) prepared from NOD mice and stimulated with the pro-inflammatory agonist LPS that is recognized by Toll-like receptor (TLR) 4 on macrophages and B cells was assessed. As NOD-derived B lymphocytes are hyper-responsive to LPS in terms of CD80 (B7.1) expression, it was demonstrated that this response is attenuated by cSN50 (FIG. 1B).

Expression of islet-toxic cytokines TNF-α, IL-1α, and IL-1β in BMDM obtained from NOD mice was suppressed. Thus, a Nuclear Transport Modifier attenuates production of islet-toxic, pro-apoptotic mediators evoked by TCR and TLR agonists in primary immune cells derived from NOD mice (FIG. 1C).

Example 3

Intracellular delivery of a Nuclear Transport Modifier to the pancreas reduces islet inflammation (insulitis). The highly effective suppression of pro-inflammatory and pro-apoptotic cytokines in ex vivo analysis of primary, NOD-derived immune cells following treatment with cSN50 peptide encouraged in vivo study of Type 1 diabetes in NOD mice. It was first determined whether cSN50 would be delivered to the pancreas, the primary site of autoimmune attack against beta cells in pancreatic islets. It was demonstrated that this cell-penetrating Nuclear Transport Modifier peptide is delivered to blood leukocytes/lymphocytes, spleen, liver, and lung to suppress acute liver and lung inflammation (Lin et al. (1995) J Biol Chem 270: 14255-14258; Liu et al. (2000) J Biol Chem 275: 16774-16778; Liu et al. (2009) Mol Ther 17: 796-802). Using confocal microscopy, the pancreatic delivery of FITC-labeled cSN50 peptide following a single intraperitoneal (i.p.) injection was assessed. Rapid and uniform intracellular delivery of FITC-cSN50 was apparent throughout the pancreas within 2 h after injection (FIG. 2A).

In vivo intracellular delivery of a Nuclear Transport Modifier to the pancreas attenuates insulitis. cSN50 was conjugated to FITC per the manufacturer's instruction. Animals received one i.p. injection of FITC-cSN50 or an amount of FITC of equivalent relative fluorescence. Animals were euthanized after 2 h and 10 μm frozen sections were cut and assessed by confocal microscopy. The cSN50-FITC peptide is distributed throughout the pancreas. In contrast, FITC alone did not penetrate the organ and only the autofluorescent tissue border is seen. Pancreas is shown at 40× magnification. (FIG. 2A).

The effect of cSN50 delivery on the ongoing insulitis was investigated. The well-characterized accelerated model of autoimmune diabetes in the NOD mouse following a single bolus of cyclophosphamide (Cy), which synchronizes progression of T1D, was selected. In this animal model of human Type 1 diabetes, two to four days following Cy injection a peak pro-inflammatory cytokine response is reported, which is followed by development of overt autoimmune diabetes in 2-4 weeks. Therefore, 10-week old female NOD mice received a single injection of Cy in two groups of seven. Treatment with cSN50 or control (either a non-cell penetrating peptide denoted cN50 or saline) was initiated 45 h later. To assure a steady level of Nuclear Transport Modifier in blood and pancreas (see FIG. 2A), a high intensity treatment protocol was adopted. 35 μg/g of cSN50 was administered i.p. every two hours for the next 24 h. The mice receiving the control peptide received a molar equivalent. Pancreatic sections were analyzed by immunohistochemistry (FIGS. 2B-D). Strikingly, 57% of treated mice following one-day therapy with cSN50 were free of insulitis while significant insulitis remained in all age-matched controls receiving Cy alone (p<0.05 vs. treated). The control finding compares well with other reports of insulitis at this age which find nearly 100% of NOD mice to demonstrate insulitis affecting a significant number of pancreatic islets.

cSN50 therapy attenuates ongoing insulitis. (FIGS. 2B, 2C, and 2D). 10 week-old NOD females received one injection of Cy (0.2 mg/g). 45 h after this injection, treatment was begun with cSN50 (35 μg/g every two hours) and continued for 24 h at which time the seven animals in each group (treatment and control) were euthanized and pancreata obtained. Sections were stained for CD3-PE (red) (FIG. 2B) and B220 (green) (FIG. 2C). The differential interference contrast (DIC or Nomarski) image is shown in FIG. 2D. Of 7 animals assessed in each group, four NOD mice receiving cSN50 were completely insulitis free as compared to persistent insulitis in all control group animals (p<0.05, chi-square).

All NOD mice receiving histologic evaluation in cSN50-treated and control groups (n=7 for each) were assigned insulitis scores based on the severity of inflammation (0=no invading cells, 1=peri-insulits, 2=invasive insulitis, 3=minimal residual islet tissue). Comparison of control to cSN50-treated animals shows significantly more unaffected islets in treated mice (*p<0.05) and significantly fewer severely affected islets (**p<0.001). (FIG. 2E). Mean insulitis score was also determined and showed a value of 0.49 in the cSN50-treated group and 1.81 in the control group (p=0.001, Mann-Whitney U test).

One year after the short-course treatment, three treated mice were also analyzed histologically for insulin production and insulitis. Sections were stained with a combination of anti-insulin FITC (green) and a combination of anti-CD3 and anti-B220PE (red). (FIG. 2F). In long-term survivors (right), insulin staining is detected but insulitis was not observed (FIG. 2F). As a staining control, islets from 15 week old control NODs show significant insulitis. Thus, a short-term intracellular delivery of cSN50 to the pancreas is followed by a rapid reversal of ongoing insulitis that is otherwise exacerbated in untreated NOD mice when T1D is synchronized with Cy.

Example 4

Islet-reactive T cells are reduced and AICD is enhanced by intracellular delivery of a Nuclear Transport Modifier. Ongoing insulitis, as a hallmark of T1D in NOD mice, is driven in part by the persistence of activated, autoreactive T and B lymphocytes. They are resistant to AICD, a critical mechanism for the loss of peripheral T cell tolerance. T- and B-lymphocytes were eliminated in the islets of cSN50-treated NOD mice (FIGS. 2B and 2C). Therefore, intracellularly delivered cSN50 may enhance lymphocyte sensitivity to AICD, thereby reversing the known resistance of NOD lymphocytes to this process. Changes in total lymphocyte numbers above the transient cell loss following Cy exposure were not observed (data not shown), however autoreactive cells may have been depleted following intense short-term treatment with the Nuclear Transport Modifier.

Adoptive transfer of islet-reactive BDC2.5 lymphocytes was utilized to test their persistence and expansion in pancreatic lymph nodes during treatment with the Nuclear Transport Modifier. Autoreactive T cells disappeared following in vivo treatment with a Nuclear Transport Modifier. Donor cells were labeled with CFSE and transferred to recipients that received cSN50 or saline continuously via osmotic pump for 4 days (FIG. 3A). Twenty million CFSE-labeled BDC2.5 splenocytes were transferred to pre-diabetic NOD recipients who received cSN50 peptide or saline by osmotic pump. (FIG. 3A). On day 4 post-transfer, pancreatic lymph node cells were harvested and the proliferation profile of CD4+Thy1.1-cells (FIG. 3B) and absolute number of CFSE+Vβ4+ cells (FIG. 3C) within the CD4 compartment was determined. Figures are representative of three separate experiments. Analysis of the pancreatic lymph node demonstrated a striking reduction in transferred islet-reactive cells in the cSN50-treated mice, as demonstrated by a significant decrease in the absolute number of CFSE-labeled, Vβ4+ cells (*p<0.05, student's t-test) recovered at the end of treatment. Islet-reactive BDC2.5 lymphocytes were precipitously reduced following cSN50 peptide treatment either by an effect on cell proliferation, lymphocyte survival, or lymphocyte entry to the node.

The effect of the Nuclear Transport Modifier on cell survival and proliferation was assessed by analyzing the sensitivity of NOD lymphocytes to AICD in an ex vivo assay. Splenocytes were harvested from 10 week old NOD females and stimulated with a defined concentration of anti-CD3/CD28 for 65 h in the presence or absence of cSN50 before detection of apoptosis with annexin-V staining (FIG. 4A). The focus was on the detection of apoptosis in NOD lymphocytes with definitive evidence of activation as determined by the achievement of at least one cell division.

Activation-induced cell death (AICD) is enhanced following ex vivo intracellular delivery of a Nuclear Transport Modifier to splenocytes. Splenocytes from 10 week-old NOD females were labeled with CFSE and stimulated with anti-CD3 (0.05 µg/ml or 2 µg/ml) and anti-CD28 (1 µg/ml) in the presence or absence of cSN50 (30 µM). After 65 h of culture, samples were harvested and labeled with annexin V-PE, anti-CD8 PerCP, and anti-CD4 APC. For analysis of AICD, activation was defined as the achievement of at least one round of division as determined by CFSE-dilution; a representative gating strategy is shown in (FIG. 4A); the undivided peak is highlighted in green and derived from unstimulated cells in the same experiment.

Figure 4B:
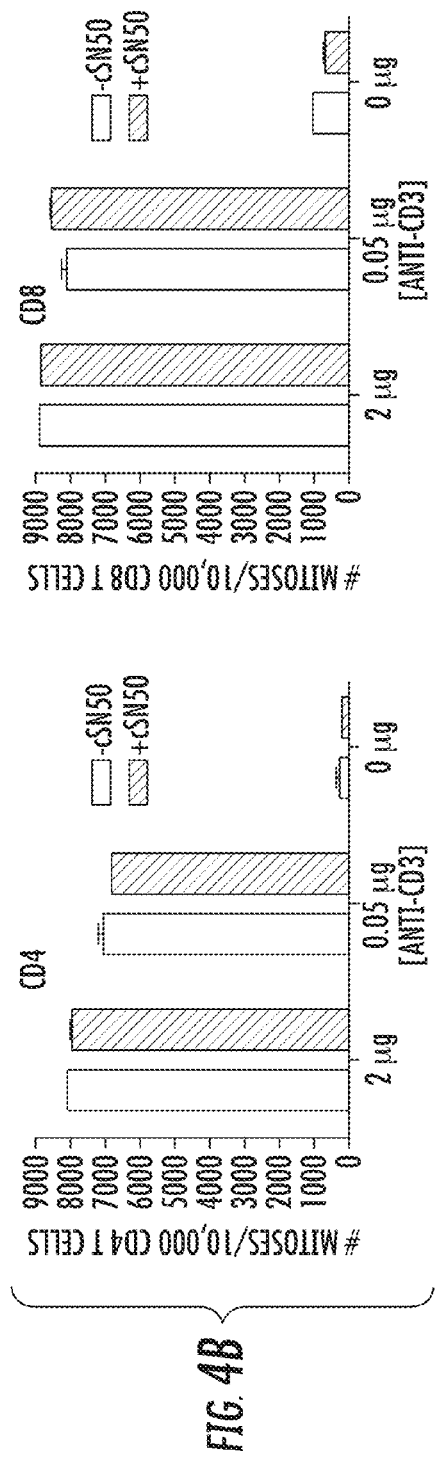

Use of CFSE to calculate the number of mitotic events following anti-CD3/CD28 stimulation revealed that cSN50 had no effect on CD4 or CD8 T cell proliferation (FIG. 4B). The CFSE division history, represented graphically as the number of mitoses per 10,000 CD4 or CD8 T cells, demonstrated no change in proliferation in CD4 or CD8 T cells in the presence of cSN50 (p=NS) (FIG. 4B).

Figure 4C:
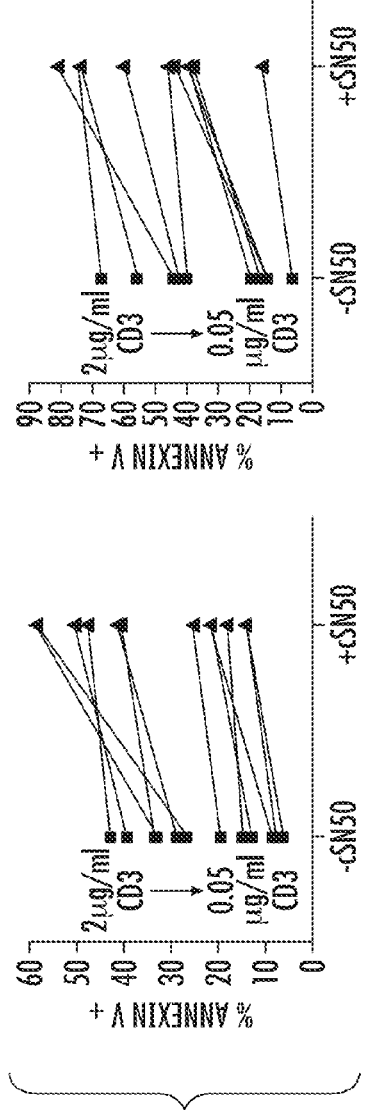

In contrast, intracellular delivery of cSN50 increased the sensitivity to AICD in CD3/CD28-stimulated CD4+ and CD8+ T cells (FIG. 4C). Further analysis revealed increased annexin-V staining on activated cells, indicative of cellular apoptosis, for cSN50-treated CD4 and CD8 T cells (p<0.005, paired student's t-test). Data is representative of at least 4 separate experiments (FIG. 4C).

Figure 5A:
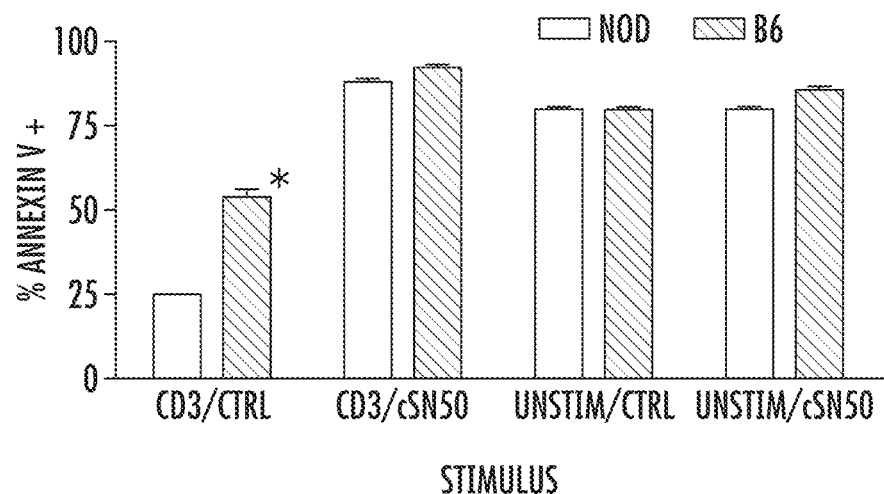
FIGS. 5A and 5B show that cSN50 restores activation-induced cell death (apoptosis) in NOD CD4 T cells and enhances B cell apoptosis in response to LPS. Splenocytes from 10-week-old NOD or C57BL/6 female mice were isolated and stimulated with anti-CD3/28 (2 µg/ml) or 5 µg/ml LPS in the presence or absence of cSN50 (30 µM). After 70 h culture, cells were harvested and apoptosis was detected by annexin V PE staining with lymphocyte co-labeling with either anti-CD4 APC (FIG. 5A) or anti-CD19 APC (FIG. 5B). NOD splenocytes when stimulated with anti-CD3/28 showed reduced apoptosis as compared to C57BL/6 splenocytes as previously published (*$p<0.01$, t-test). Addition of cSN50 normalized apoptosis to C57BL/6 levels (p=NS). Unstimulated lymphocytes showed high levels of apoptosis, as expected for unactivated lymphocytes in culture; this process was not enhanced by cSN50 (FIG. 5A). Exposure to cSN50 significantly enhanced sensitivity to cell death in LPS-stimulated B lymphocytes ($p<0.005$, paired Student's t-test) (FIG. 5B).

As anticipated, CD4 T cells from NOD mice were generally more resistant to AICD but following cSN50 peptide delivery, they displayed a significant increase in sensitivity to AICD; in fact, the percentage of CD4 T cells undergoing AICD reached values comparable to T cells obtained from the non-diabetes prone C57BL/6 strain (FIG. 5A). NOD splenocytes when stimulated with anti-CD3/28 showed reduced apoptosis as compared to C57BL/6 splenocytes as previously published (*p<0.01, t-test) (FIG. 5A). Addition of cSN50 normalized apoptosis to C57BL/6 levels (p=NS). Unstimulated lymphocytes showed high levels of apoptosis, as expected for unactivated lymphocytes in culture; this process was not enhanced by cSN50.

Figure 5B:
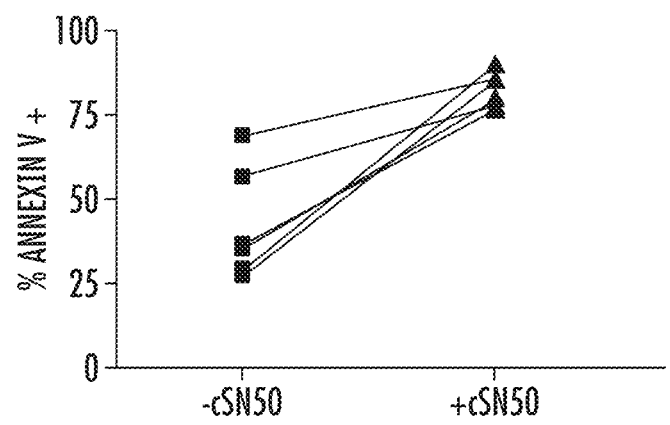

In parallel to the significant change in sensitivity to AICD noted in NOD mice-derived T cells, B lymphocytes also had an increase in sensitivity to apoptosis induced by their agonist in the presence of cSN50 peptide. When B cells were analyzed with similar methods following stimulation with the TLR4 agonist, LPS, they displayed enhanced propensity for cell death (p<0.005, paired Student's t-test) (FIG. 5B). Thus, the cSN50 not only reduced the number of islet-reactive T cells but restored sensitivity to activation-induced cell death (apoptosis) in NOD CD4 T cells and enhances B cell apoptosis in response to LPS. Splenocytes from 10-week-old NOD or C57BL/6 female mice were isolated and stimulated with anti-CD3/28 (2 µg/ml) or 5 µg/ml LPS in the presence or absence of cSN50 (30 µM). After 70 h culture, cells were harvested and apoptosis was detected by annexin V PE staining with lymphocyte co-labeling with either anti-CD4 APC (FIG. 5A) or anti-CD19 APC (FIG. 5B).

Example 5

Figure 6A:
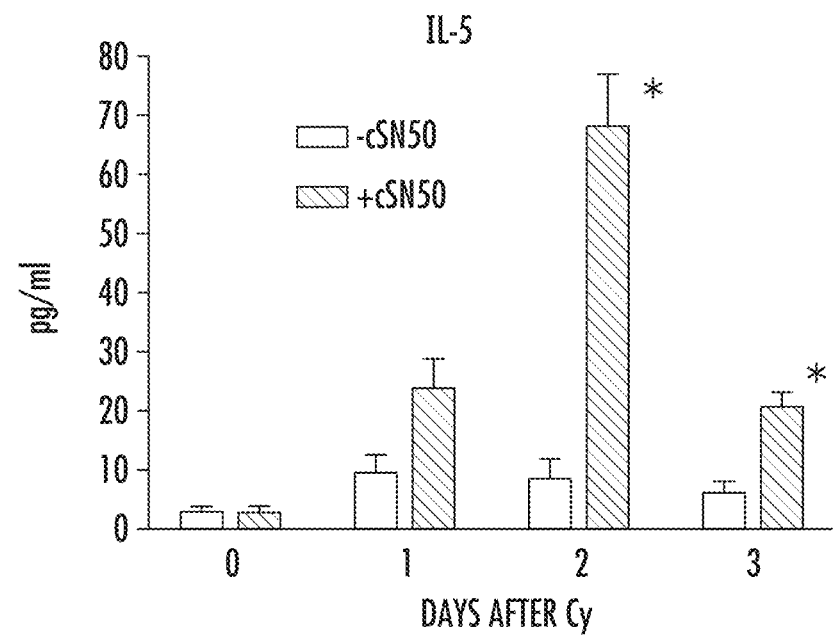
FIGS. 6A and 6B show that expression of immunomodulatory cytokines IL-5 and IL-10 is modified during treatment with a Nuclear Transport Modifier. Blood samples were obtained daily by saphenous vein bleeding beginning on the day of Cy challenge. Cytokine levels in plasma were determined by cytokine bead array and comparison to a standard curve. cSN50-treated mice demonstrate increased IL-5 ($p<0.05$ ANOVA; subsequent analysis of individual days by Student's t-test shows *$p<0.05$ for days 2 and 3) during therapy (FIG. 6A). Splenocytes from 10 week-old NOD females that had received cyclophosphamide were harvested after 24 hr of treatment with cSN50 or control non-cell-penetrating peptide (cN50) and restimulated with LPS to assess their cytokine profile. Supernatants were harvested at 72 h and analyzed by cytokine bead array for presence of IL-10. Splenocytes from cSN50 treated animals produced increased levels IL-10 (*$p<0.05$) (FIG. 6B). Data are from three separate experiments.

Immunomodulatory Cytokines IL-5 and IL-10 are enhanced in animals treated with a Nuclear Transport Modifier. Although cSN50 treatment eliminated the majority of islet-reactive lymphocytes and facilitated reduction of insulitis, these islet-reactive and invading immune cells did not completely vanish following intense 1- or 4-day delivery of cSN50 peptide via i.p. injection or osmotic pump, respectively. Therefore, it was considered whether there had been augmentation in regulatory cells or whether the remaining lymphocytes demonstrate alteration in their cytokine expression profile. Analysis of the absolute number of regulatory T cells was determined by intracellular Foxp3 staining and showed no difference between treated and control mice at either the end of treatment (48 h) or two weeks after treatment concluded. With respect to cytokine expression, the systemic effect of cSN50 on cytokines/chemokine production in blood of NOD mice was monitored daily in plasma samples in treated and control mice beginning on the day of Cy administration until 12 days following peptide treatment (day 14 post-Cy bolus). During this period of administration, increased circulating levels of IL-5 were detected on day 2 after Cy administration (FIG. 6A). No differences were detected in plasma levels of TNF-α, IFN-γ, IL-10, IL-12, IL-2, or IL-4, Eotaxin, GM-CSF, IL-1α, IL-1β, M-CSF, IL-3, IL-7, IL-9, IL-12 (p40), IL-12 (p70), IL-13, IL-15, IL-17, IP-10, MIP-2, KC, LIF, LIX, MIP-1α, MIP-1β, MIG, RANTES, or VEGF (data not shown) and most of these markers of inflammation were barely detectable in plasma or were below the limit of detection.

Expression of immunomodulatory cytokines IL-5 and IL-10 is modified during treatment with a Nuclear Transport Modifier. Blood samples were obtained daily by saphenous vein bleeding beginning on the day of Cy challenge. Cytokine levels in plasma were determined by cytokine bead array and comparison to a standard curve. cSN50-treated mice demonstrate increased IL-5 (p<0.05 ANOVA; subsequent analysis of individual days by Student's t-test shows *p<0.05 for days 2 and 3) during therapy (FIG. 6A).

Figure 6B:
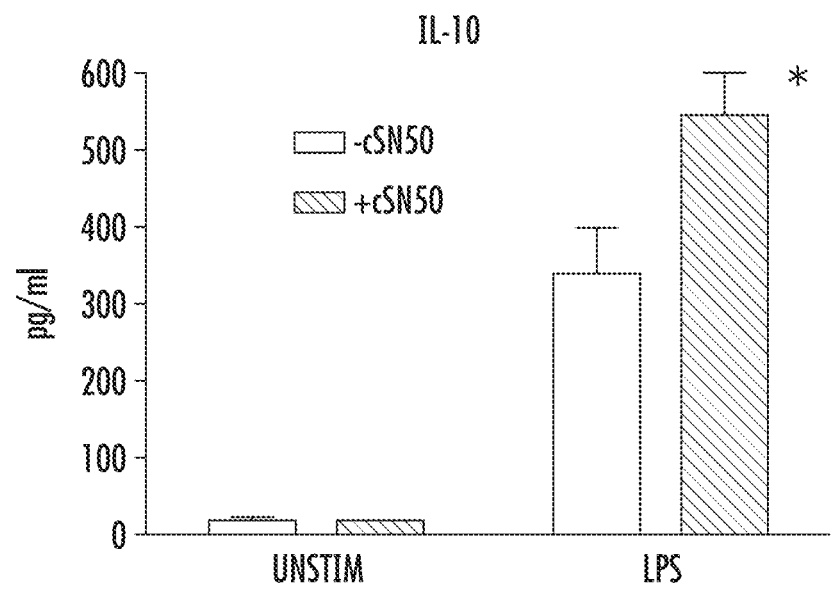

It was considered that the capacity for production of anti-inflammatory cytokines may have been modified although increased systemic production of anti-inflammatory cytokines, such as IL-10, was not detected. Therefore, splenocytes from NOD females that had received 24-h peptide therapy beginning two days after Cy acceleration were obtained to examine the effect of cSN50 peptide on ex vivo cytokine production by immune cells. Splenocytes from 10 week-old NOD females that had received cyclophosphamide were harvested after 24 hr of treatment with cSN50 or control non-cell-penetrating peptide (cN50) and restimulated with LPS to assess their cytokine profile. Supernatants were harvested at 72 h and analyzed by cytokine bead array for presence of IL-10. Splenocytes from cSN50 treated animals produced increased levels IL-10 (*p<0.05) (FIG. 6B). Data are from three separate experiments. Restimulated splenocytes from treated animals showed increased production of the anti-inflammatory cytokine IL-10 suggesting that cSN50 peptide was not simply a global suppressant of pro-inflammatory cytokine/chemokine production in NOD mice but rather a modulator of lymphocyte function in lymphoid organs (FIG. 6B).

Together with results depicted in FIG. 1, these cumulative data indicate the ability of a Nuclear Transport Modifier to exert a bimodal effect on primary NOD immune cells by suppressing the expression of pro-inflammatory mediators, including islet-toxic cytokines like IFN-γ and TNF-α while preserving or enhancing anti-inflammatory cytokines, such as IL-10 and Transforming Growth Factor beta, that are likely associated with recovery of regulatory T cells (Tregs) following treatment with NTM. This reprogramming effect is likely to contribute to the restoration of peripheral tolerance to autoantigens.

Example 6

Figure 7:
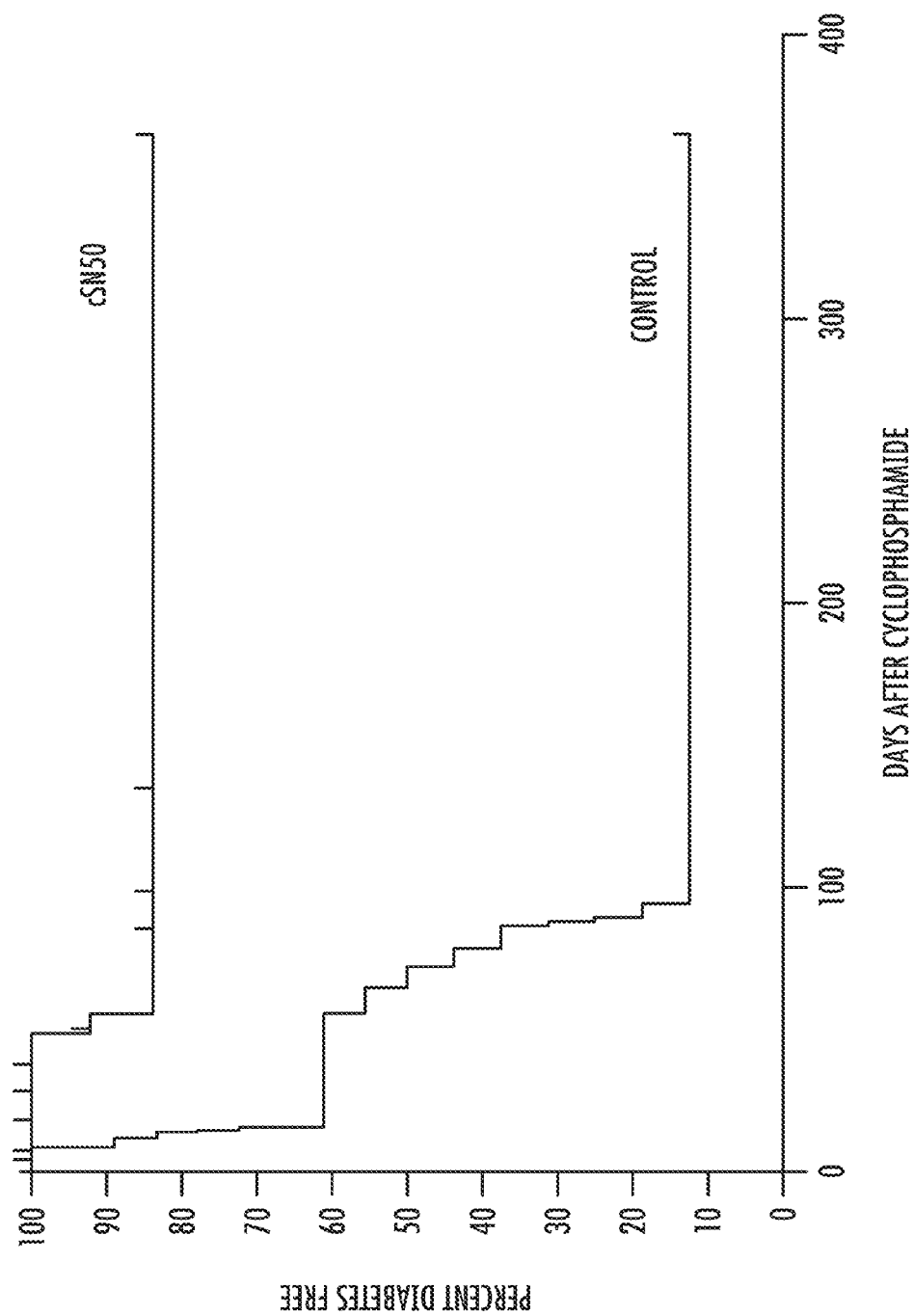
FIG. 7 shows that short-term intracellular delivery of a Nuclear Transport Modifier in vivo protects NOD mice from autoimmune diabetes for over one year. Ten week old female NOD mice received one dose of Cy (0.2 mg/g) to synchronize autoimmune diabetes progression. After 45 h, intracellular peptide delivery was initiated with cSN50 (35 µg/g) or with control and continued every 2 h for 48 h. Blood glucose was assessed twice weekly. cSN50-treated mice (n=20) were significantly protected from diabetes progression as compared to saline-treated control (n=10, $p<0.0001$) or the non-cell-penetrating peptide cN50-treated control (n=10, $p=0.006$). A comparison of cSN50-treated vs. the combined control groups as illustrated in FIG. 7 also demonstrated significant protection ($p=0.0002$, log-rank test).

Short-term intracellular delivery of a Nuclear Transport Modifier in vivo protects NOD mice from autoimmune diabetes for over one year (FIG. 7). A striking effect of in vivo delivery of cSN50 peptide on reversal of insulitis through reduction of islet-reactive T and B cells was established. A pre-clinical study of cSN50 peptide in terms of its effect on T1D progression was performed.

Ten week old female NOD mice received one dose of Cy (0.2 mg/g) to synchronize autoimmune diabetes progression. After 45 h, a high intensity treatment protocol was utilized to assure a steady level of Nuclear Transport Modifier in blood and pancreas; control mice received saline or control peptide at molar equivalent. Intracellular peptide delivery was initiated with cSN50 (35 μg/g) or with control and continued every 2 h for 48 h. Blood glucose was assessed twice weekly. cSN50-treated mice (n=20) were significantly protected from diabetes progression as compared to saline-treated control (n=10, p<0.0001) or the non-cell-penetrating peptide cN50-treated control (n=10, p=0.006). A comparison of cSN50-treated vs. the combined control groups as illustrated in FIG. 7 also demonstrated significant protection (p=0.0002, log-rank test).

Figure 8A:
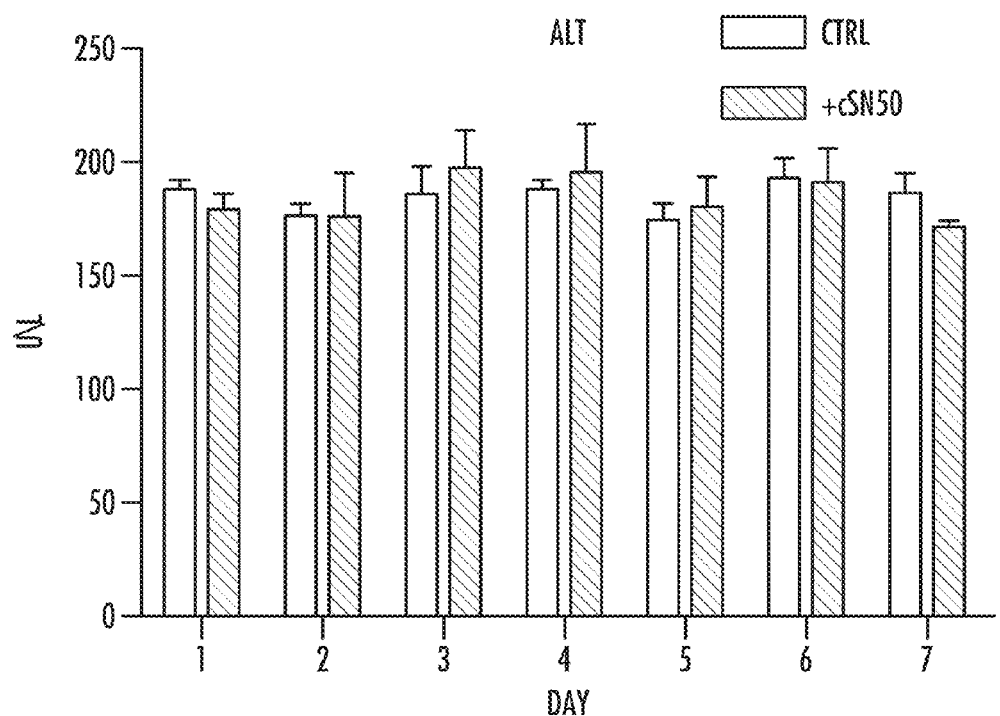
FIGS. 8A and 8B shows that short-term treatment of NOD mice with a Nuclear Transport Modifier shows no effect on measured clinical biomarkers of liver and kidney toxicity. Ten week old female NOD mice received one dose of Cy (0.2 mg/g); after 45 h, intracellular peptide delivery was initiated with cSN50 (35 µg/g) or with control cN50 and continued every 2 h for 48 h. Serum was obtained daily from the saphenous vein and measurements of ALT (FIG. 8A) and BUN (FIG. 8B) were performed in 7 mice in each group. No significant differences were determined. Measurements for alkaline phosphatase, creatinine, creatine kinase, and total bilirubin were below the limit of detection in both groups.
Figure 8B:
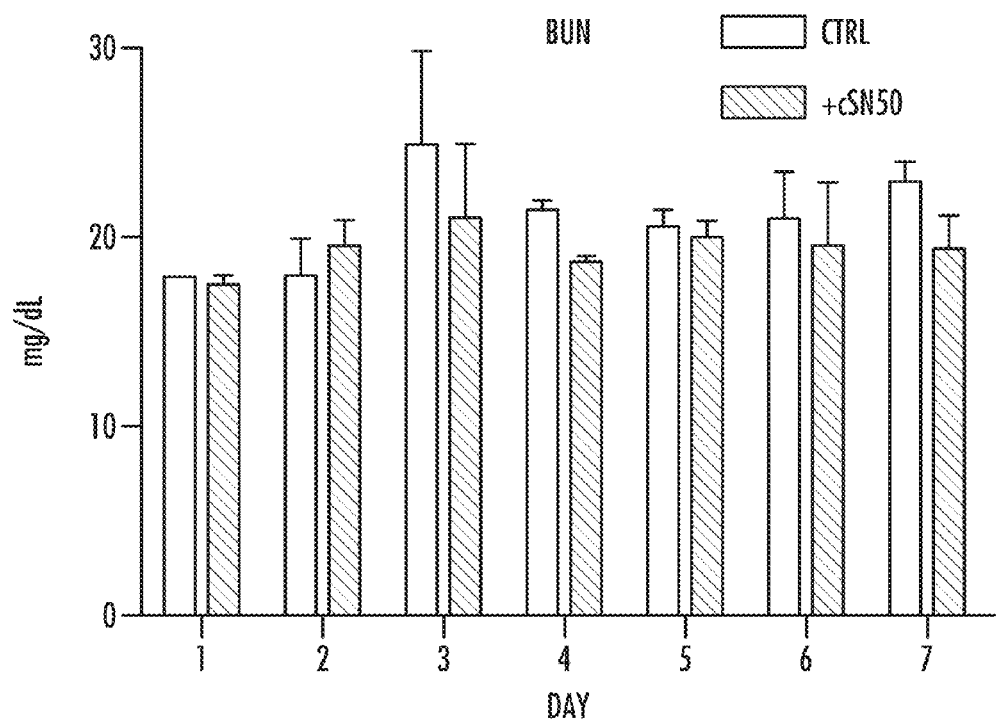

As documented in FIG. 7, the majority of NOD mice (90%) were rendered diabetes-free following this short-term treatment of only 2 days with cSN50. In contrast, 90% of control mice developed diabetes by 100 days after Cy bolus. The progression to diabetes in control group proceeded in two phases. On days 10-30, a first wave of diabetes developed and cSN50 afforded 100% protection against this process. In the second wave, corresponding closely to the normal progression of spontaneous diabetes between days 60-100 post-Cy (ages 18-23 weeks), protection was incomplete but still substantial even though more than two months had elapsed since the last dose of Nuclear Transport Modifier. Strikingly, the cSN50 peptide-treated mice remained euglycemic, which obviated the need for insulin replacement therapy. Importantly, they did not display overt signs of toxicity during 365 days of observation. The lack of toxicity of intensive treatment in this model was supported by normal weight gain, no signs of acquired infection, and normal clinical chemistries (ALT and BUN levels were not significantly different from control, FIGS. 8A and 8B).

Short-term treatment of NOD mice with a Nuclear Transport Modifier shows no effect on measured clinical biomarkers of liver and kidney toxicity. Ten week old female NOD mice received one dose of Cy (0.2 mg/g); after 45 h, intracellular peptide delivery was initiated with cSN50 (35 μg/g) or with control cN50 and continued every 2 h for 48 h. Serum was obtained daily from the saphenous vein and measurements of ALT (FIG. 8A) and BUN (FIG. 8B) were performed in 7 mice in each group. No significant differences were determined. Measurements for alkaline phosphatase, creatinine, creatine kinase, and total bilirubin were below the limit of detection in both groups.

Moreover, anti-cSN50 peptide antibody induction in an ELISA assay was not detected where the limit of detection based on a titration of cSN50-reactive IgG antibody was 10 ng/mL (O.D. values for serum were not significantly different from secondary antibody alone).

Thus, short-term targeting of the nuclear import of stress-responsive transcription factors with cSN50 peptide suppressed accelerated autoimmune diabetes progression and rendered thriving NOD mice free of diabetes progression for at least one year.

Example 7

Islet cell transplantation will be performed in order to provide insulin producing capability to an individual with Type 1 Diabetes whose beta cells within the pancreatic islets no longer produce insulin. In islet transplantation, islets are taken from the pancreas of a deceased donor. Typically, a subject will receive 10,000 islet equivalents per kilogram of body weight. After transplantation, the beta cells in the islets will begin to make and release insulin. The subject may require two transplants to achieve insulin independence. Donor antigen presenting cells may be removed from the islets before transplantation (Huang et al., (2008) Endocrine Reviews 29(5): 603-630). The beta cells of the islets will be stored and transported in a composition comprising cSN50 or cSN50.1 after removal from the donor and before implantation into the recipient. The composition comprising cSN50 or cSN50.1 may be added to the islets during the isolation process from the donor.

Example 8

Islet cell transplantation will be performed in order to provide insulin producing capability to an individual with Type 1 Diabetes whose beta cells within the pancreatic islets no longer produce insulin. In islet transplantation, islets are taken from the pancreas of a deceased donor. Typically, a subject will receive 10,000 islet equivalents per kilogram of body weight. After transplantation via portal vein into liver, the beta cells in the islets will begin to make and release insulin. The subject may require two transplants to achieve insulin independence. A composition comprising cSN50 and cSN50.1 may be administered to the recipient before and after islet transplantation. Treatments with cSN50 and cSN50.1 may be administered during treatment with growth factors (Huang et al., (2008) Endocrine Reviews 29(5): 603-630). Variations and modifications to the preferred embodiments of the invention described herein will be apparent to those skilled in the art. It is intended that such variations and modifications may be made without departing from the scope of the invention and without diminishing its attendant advantages.

Other Embodiments

Any improvement may be made in part or all of the compositions, kits, cells, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A composition comprising a pharmaceutically acceptable carrier and a therapeutically effective amount of a Nuclear Transport Modifier comprising a sequence selected from the group consisting of:
SEQ ID NO: 2, SEQ ID NO: 5, SEQ ID NO: 6, and SEQ ID NO: 7, wherein Xaa is any amino acid or absent.

2. The composition of claim 1, wherein the Nuclear Transport Modifier is cSN50.1 having the sequence set forth in SEQ ID NO: 2.

3. The composition of claim 1, wherein the therapeutically effective amount is sufficient for preserving viability of insulin-producing beta cells and insulin-producing capacity of the cells in a subject.

4. The composition of claim 1, wherein the therapeutically effective amount is sufficient for treating Diabetes in a subject.

5. The composition of claim 4, wherein the Diabetes is Type 1 or Type 2 Diabetes.

6. Insulin-producing beta cells comprising a Nuclear Transport Modifier comprising a sequence selected from the group consisting of:
SEQ ID NO: 2, SEQ ID NO: 5, SEQ ID NO: 6, and SEQ ID NO: 7, wherein Xaa is any amino acid or absent.

7. The insulin-producing beta cells of claim 6, wherein the Nuclear Transport Modifier is cSN50.1 having the sequence set forth in SEQ ID NO: 2.

8. The insulin-producing beta cells of claim 6, wherein the Nuclear Transport Modifier is in an amount sufficient for decreasing autoimmune inflammation-induced apoptosis of the population of insulin-producing beta cells.

9. The insulin-producing beta cells of claim 6, wherein the Nuclear Transport Modifier is in an amount sufficient for decreasing metabolic inflammation-induced apoptosis of the population of insulin-producing beta cells.

10. The insulin-producing beta cells of claim 6, wherein the Nuclear Transport Modifier is in an amount sufficient for preserving viability of the insulin-producing beta cells and insulin-producing capacity of the insulin-producing beta cells.

11. The composition of claim 1, wherein the Nuclear Transport Modifier has the sequence set forth in SEQ ID NO: 5.

12. The composition of claim 1, wherein the Nuclear Transport Modifier has the sequence set forth in SEQ ID NO: 7.

13. The insulin-producing beta cells of claim 6, wherein the Nuclear Transport Modifier has the sequence set forth in SEQ ID NO: 5.

14. The insulin-producing beta cells of claim 6, wherein the Nuclear Transport Modifier has the sequence set forth in SEQ ID NO: 7.

* * * * *